(12) United States Patent
Tsai et al.

(10) Patent No.: US 8,536,406 B2
(45) Date of Patent: Sep. 17, 2013

(54) COMT1 GENE FIBER-SPECIFIC PROMOTER ELEMENTS FROM POPLAR

(75) Inventors: Chung-Jui Tsai, Athens, GA (US); Edward Odhiambo Anino, Suna Migori (KE)

(73) Assignee: Michigan Technological University, Houghton, MI (US)

(*) Notice: Subject to any disclaimer, the term of this patent is extended or adjusted under 35 U.S.C. 154(b) by 276 days.

(21) Appl. No.: 12/990,001

(22) PCT Filed: Apr. 28, 2009

(86) PCT No.: PCT/US2009/041956
§ 371 (c)(1),
(2), (4) Date: Oct. 28, 2010

(87) PCT Pub. No.: WO2009/134785
PCT Pub. Date: Nov. 5, 2009

(65) Prior Publication Data
US 2011/0041211 A1 Feb. 17, 2011

Related U.S. Application Data

(60) Provisional application No. 61/048,435, filed on Apr. 28, 2008.

(51) Int. Cl.
*C12N 15/82* (2006.01)
*A01H 1/00* (2006.01)
*A01H 4/00* (2006.01)
*C07H 21/04* (2006.01)

(52) U.S. Cl.
USPC .......... 800/287; 800/278; 800/284; 800/295; 800/298; 536/24.1; 536/23.2; 536/23.6

(58) Field of Classification Search
None
See application file for complete search history.

(56) References Cited

U.S. PATENT DOCUMENTS

| 3,067,099 A | 12/1962 | McCormick et al. |
| 4,683,195 A | 7/1987 | Mullis et al. |
| 4,683,202 A | 7/1987 | Mullis |
| 4,795,855 A | 1/1989 | Fillatti et al. |
| 5,004,863 A | 4/1991 | Umbeck |

(Continued)

FOREIGN PATENT DOCUMENTS

| CA | 2005597 | 6/1990 |
| WO | 9204449 | 3/1992 |

(Continued)

OTHER PUBLICATIONS

Hayakawa et al. Molecular cloning and tissue-specific expression of two genes that encode caffeic acid O-methyltransferase from *Populus kitakamiensis*. Plant Science. 1996. 113(2): 157-165.*

(Continued)

*Primary Examiner* — Cathy Kingdon Worley
*Assistant Examiner* — Ashley K Buran
(74) *Attorney, Agent, or Firm* — Michael Best & Friedrich LLP

(57) ABSTRACT

Polynucleotide constructs contain fiber-specific elements which are used to target expression of polynucleotides and polypeptides to the vascular fibers of a plant. The constructs can be contained within a vector. Transgenic plants transformed with the fiber-specific elements can be made which have expression of a polynucleotide or polypeptide directed to the plant fibers.

21 Claims, 7 Drawing Sheets

```
-473                                                      -414
TAAGTTCAGTAAATATAATCGGGTGAATATCTCATCATGTAATTAAATATCTTAATCTC
    YACT (- strand, YACT box)
         NGATT (- strand, ARR element)
             GTGA (+ strand, GTGA motif)
                 GATA (- strand, GATA box)
                         AATTAAA(AT rich)
                             GATA (-, GATA box)
                                 NGATT (-, ARR)
```

(56) References Cited

U.S. PATENT DOCUMENTS

| | | | |
|---|---|---|---|
| 5,097,025 A | 3/1992 | Benfey et al. | |
| 5,110,732 A | 5/1992 | Benfey et al. | |
| 5,159,135 A | 10/1992 | Umbeck | |
| 5,352,605 A | 10/1994 | Fraley et al. | |
| 5,362,865 A | 11/1994 | Austin | |
| 5,378,619 A | 1/1995 | Rogers | |
| 5,416,011 A | 5/1995 | Hinchee et al. | |
| 5,451,514 A | 9/1995 | Boudet et al. | |
| 5,463,174 A | 10/1995 | Moloney et al. | |
| 5,463,175 A | 10/1995 | Barry et al. | |
| 5,518,908 A | 5/1996 | Corbin et al. | |
| 5,569,834 A | 10/1996 | Hinchee et al. | |
| 5,593,874 A | 1/1997 | Brown et al. | |
| 5,633,435 A | 5/1997 | Barry et al. | |
| 5,730,986 A | 3/1998 | Bandyopadhyay et al. | |
| 5,859,347 A | 1/1999 | Brown et al. | |
| 5,922,928 A | 7/1999 | Chiang et al. | |
| 6,455,762 B1 | 9/2002 | Chiang et al. | |
| 7,064,246 B2* | 6/2006 | MacRae | 800/291 |
| 7,361,806 B2* | 4/2008 | Lebel et al. | 800/288 |
| 2002/0138870 A1 | 9/2002 | Chiang et al. | |
| 2008/0196125 A1* | 8/2008 | Papes et al. | 800/298 |
| 2009/0229016 A2* | 9/2009 | Papes et al. | 800/298 |
| 2011/0041211 A1 | 2/2011 | Tsai | |

FOREIGN PATENT DOCUMENTS

| | | |
|---|---|---|
| WO | 9305160 | 3/1993 |
| WO | 9319189 | 9/1993 |
| WO | 9423018 | 10/1994 |
| WO | 9743430 | 11/1997 |
| WO | 9961631 | 12/1999 |
| WO | 0127241 | 4/2001 |
| WO | 2005096805 | 10/2005 |
| WO | 2008069878 | 6/2008 |
| WO | 2009134785 | 11/2009 |

OTHER PUBLICATIONS

Tiimonen et al. The seasonal activity and the effect of mechanical bending and wounding on the PtCOMT promoter in *Betula pendula* Roth. Plant Cell Rep. 2007. 26: 1205-1214.*

Abe et al., "*Arabidopsis* AtMYC2 (bHLH) and AtMYB2 (MYB) Function as Transcriptional Activators in Abscisic Acid Signaling," Plant Cell (2003) 15:63-78.

Advisory Committee on Novel Foods and Processes, Report on the Use of Antibiotic Resistance Markers in Genetically Modified Food Organisms, (Jul. 1994) 46 pgs.

Aitchitt et al., "A Rapid and Efficient Method for the Extraction of Total DNA from Mature Leaves of the Date Palm (*Phoenix dactylifera* L.)," Plant Mol. Biol. Reporter (1993) 11:4:317-319.

Alberts et al., Molekularbiologie der Zelle (Molecular Biology of the Cell), 2nd Edition, VCH Verlag (1989) (pp. 1198-1237)—BOOK.

Allina et al., "4¬Coumarate:Coenzyme A Ligase in Hybrid Poplar," Plant Physiol. (1998) 116:743-754.

Allwood et al., "Phosphorylation of phenylalanine ammonia-lyase: evidence for a novel protein kinase and identification of the phosphorylated residue," FEBS Letters (1999) 457:47-52.

An et al., "Functional Analysis of the 3' Control Region of the Potato Wound-Inducible Proteinase Inhibitor II Gene," Plant Cell (1989) 1:115-122.

An et al., "Organ-Specific and Developmental Regulation of the Nopaline Synthase Promoter in Transgenic Tobacco Plants," Plant Physiol. (1988) 88:547-552.

Andersson-Gunneras et al., "Biosynthesis of cellulose¬enriched tension wood in *Populus*: global analysis of transcripts and metabolites identifies biochemical and developmental regulators in secondary wall biosynthesis," Plant J. (2006) 45:144-165.

Anino, E. O., "Characterization of *Populus tremuloides* Caffeic Acid O-Methyltransferase and 4-Coumarate:CoA Ligase Gene Promoters to Identify Regulatory Elements," (2008) Ph.D. dissertation, Michigan Technological University.

Appert et al., "Structural and catalytic properties of the four phenylalanine ammonia-lyase isoenzymes from parsley (*Petroselinum crispum* Nym.)," Eur. J. Biochem. (1994) 225:491-499.

Artsaenko et al., "Expression of a Single-Chain Fv Antibody Against Abscisic Acid Creates a Wilty Phenotype in Transgenic Tobacco," Plant J. (1995) 8(5):745-750.

Aryan et al., "Structural and Functional Analysis of Promoter from Gliadin, an Endosperm-Specific Storage Protein Gene of *Triticum aestivum* L.," Mol. Gen. Genet. (1991) 225:65-71.

Atchison et al., "Enhancers: Mechanisms of Action and Cell Specificity," Am. Rev. Cell Biol., (1988) 4:127-153.

Ausubel et al., "Short Protocols in Molecular Biology," A Compendium of Methods from Current Protocols in Molecular Biology, (1989)—BOOK.

Bailey et al., "Unsupervised Learning of Multiple Motifs in Biopolymers Using Expectation Maximization," Dept. Computer Sci. Univ. California San Diego (1995) 1-37.

Baucher et al., "Red Xylem and Higher Lignin Extractability by Down-Regulating a Cinnamyl Alcohol Dehydrogenase in Poplar," Plant Physiol. (1996) 112:1479-1490.

Bauer et al., "Identification of differentially expressed mRNA species by an improved display technique (DDRT-PCR)," Nuc. Acid. Res. (1993) 21:4272-4280.

Beaucage et al., "Deoxynucleoside Phosphoramidites—A New Class of Key Intermediates for Deoxypolynucleotide Synthesis," Tetrahedron Letters (1981) 22:20:1859-1862.

Becker-Andre et al., "Structural Comparison, Modes of Expression, and Putative cis-Acting Elements of the Two 4-Coumarate: CoA Ligase Genes in Potato," J. Biol. Chem. (1991) 266:8551-8559.

Bell-Lelong et al., "Cinnamate-4¬Hydroxylase Expression in *Arabidopsis*,". Plant Physiol. (1997) 113: 729-738.

Benfey, et al., "Tissue-Specific Expression from CaMV 35S Enhancer Subdomains in Early Stages of Plant Development," EMBO J. (1990) 9:6:1677-1684.

Benoist et al., "In vivo Sequence Requirements of the SV40 Early Promoter Region," Nature (1981) 290:304-310.

Bevan et al., "Tissue and Cell-Specific Activity of a Phenylalanine Ammonia-Lyase Promoter in Transgenic Plants," EMBO J. (1989) 8:7:1899-1906.

Bird et al., "Manipulation of Plant Gene Expression by Antisense RNA," Biotech. and Genetic Eng. Rev. (1991) 9:207-227.

Birren et al., "Genome Analysis, A Laboratory Manual, Analyzing DNA," (1997) 1:543—BOOK.

Birren et al., "Genome Analysis, A Laboratory Manual, Cloning Systems," (1999) vol. 3—BOOK.

Birren et al., "Genome Analysis, A Laboratory Manual, Detecting Genes," (1998) vol. 2—BOOK.

Birren et al., "Genome Analysis, A Laboratory Manual, Mapping Genomes," (1999) vol. 4—BOOK.

Bittsanszky et al., "Ability of transgenic poplars with elevated glutathione content to tolerate zinc(2+) stress," Env. Int'l. (2005) 31:251-254.

Blumer S., "Characterization of a *Populus tremuloides* 5-hydroxyconiferaldehyde O-methyltransferase (AldOMT) gene promoter," (2002) MS thesis, Michigan Technological University.

Blake et al., "Polymerase Chain Reaction Used for Monitoring Multiple Gene Integration in *Agrobacterium*-Mediated Transformation," Crop Sci. (1991) 31:1686-1688.

Boerjan et al., "Lignin Biosynthesis," Annual Rev. Plant Biol. (2003) 54:519-546.

Bolwell et al., "L-Phenylalanine ammonia-lyase from *Phaseolus vulgaris*: modulation of the levels of active enzyme by trans-cinnamic acid," Planta (1986) 169:97-107.

Bolwell, G.P., "A role for phosphorylation in the down-regulation of phenylalanine ammonia-lyase in suspension-cultured cells of french bean," Phytochem. (1992) 31:4081-4086.

Boudet et al., "Lignins and lignocellulosics: a better control of synthesis for new and improved uses," Trends in Plant Science (2003) 8: 576-581.

Boudet, et al., "Biochemistry and Molecular Biology of Lignification," New Phytol. (1995) 129:203-236.

Breathnach et al., "Organization and Expression of Eucaryotic Split Genes Coding for Proteins," Ann. Rev. Biochem. (1981) 50:349-383.

Bucholtz et al., "Lignin Biochemistry of Normal and Brown Midrib Mutant Sorghum", J. Agric. Food Chem. (1980) 28:6:1239-1241.

Bugos et al., "Characterization of Bispecific Caffeic Acid/5-Hydroxyferulic Acid O-Methyltransferase from Aspen", Phytochem. (1992) 31:51495-1498.

Bugos, et al., "Isolation of O-Methyltransferase Associated with Lignin Biosynthesis in Aspen", International Symposium on Wood and Pulping Chemistry, NC State University, Raleigh, NC (May 22-25, 1989) pp. 345-347.

Bugos et al., "RNA Isolation from Plant Tissues Recalcitrant to Extraction in Guanidine," BioTechniques (1995) 19:5:734-737.

Bugos et al., "cDNA cloning, sequence analysis and seasonal expression of lignin-bispecific caffeic acid/5-hydroxyferulic acid O-methyltransferase of aspen," Plant Mol. Biol. (1991) 17:1203-1215.

Burge et al., "Prediction of Complete Gene Structures in Human Genomic DNA," J. Mol. Biol. (1997) 268:78-94.

Bustos et al., "Regulation of β-Glucuronidase Expression in Transgenic Tobacco Plants by an A/T-Rich, cis-Acting Sequence Found Upstream of a French Bean β-Phaseolin Gene," Plant Cell (1989) 1:839-853.

Bytebier et al., "T-DNA Organization in Tumor Cultures and Transgenic Plants of the Monocotyledon Asparagus officinalis," Proc. Natl. Acad. Sci. (1987) 84:5345-5349.

Callis et al., "Heat Inducible Expression of a Chimeric Maize hsp70CAT Gene in Maize Protoplasts," Plant Physiol. (1988) 88:965-968.

Campbell et al., "Variation in Lignin Content and Composition," Plant Physiol. (1996) 110: 3-13.

Capellades et al., "The maize caffeic acid O-methyltransferase gene promoter is active in transgenic tobacco and maize plant tissues," Plant Mol. Biol.(1996) 31:307-332.

Terashima et al., "Heterogeneity in Formation of Lignin. VII. An Autoradiographic Study on the Formation of Guaiacyl and Syringyl Lignin in Poplar," J. Wood Chem. & Tech. (1986) 6:4:495-504.

Thornburg, et al., "Wound-Inducible Expression of a Potato Inhibitor II-Chloramphenicol Acetyltransferase Gene Fusion in Transgenic Tobacco Plants," Proc. Natl. Acad. Sci. (1987) 84:744-748.

Tiimonen et al., "The seasonal activity and the effect of mechanical bending and wounding on the PtCOMT promoter in Betula pendula Roth," Plant Cell Rep. (2007) 26:1205-1214.

Timell T.E., "The Chemical Composition of Tension Wood," Svensk Papperstidning (Swedish Paper Journal) (1969) 72:173-181.

Toriyama, et al., "Transgenic Rice Plants After Direct Gene Transfer into Protoplasts," Bio/Technology (1988) 6:1072-1074.

Tsai et al., "Generic Engineering of Quaking Aspen Through Agrobacterium-Mediated Transformation for Modification of Lignin Biosynthesis," Dissertation (1995).

Tsai et al., "Nucleotide sequence of a *Populus tremuloides* gene encoding bispecific caffeic acid/5-hydroxyferulic acid O-methyltransferase," Plant Physiol. (1995) 107:1459.

Tsai C-J., "Genome-wide analysis of the structural genes regulating defense phenylpropanoid metabolism in *Populus*," New Phytologist (2006) 172:47-62.

Tsai et al., "3 Cycle-labeled oligonucleotides with predictable length for primer extension and transgene analysis," Nuc. Acids Res. (1996) 24:24:5056-5061.

Tsai et al., *Agrobacterium*-mediated transformation of quaking aspen (*Populus tremuloides*) and regeneration of transgenic plants. Plant Cell Rep (1994) 14: 94-97.

Tsai et al., "*Populus tremuloides* caffeic acid/5-hydroxyferulic acid O-methyltransferase (PTOMT1) gene, complete cds," EMBL Database accession No. U13171 (1994) Abstract.

Tsai et al., "Suppression of O-methyltransferase gene by homologous sense transgene in quaking aspen causes red-brown wood phenotypes," Plant Physiol. (1998) 117:101-112.

Tuskan et al. (2006) The Genome of Black Cottonwood, *Populus trichocarpa* (Torr. & Gray). In, vol. 313, pp. 1596-1604.

Uhlmann et al., "Molecular Cloning and Expression of 4 ¬ Coumarate:Coenzyme A Ligase, an Enzyme Involved in the Resistance Response of Soybean (*Glycine max* L.) against Pathogen Attack," Plant Physiol. (1993) 102: 1147-1156.

Uimari et al., "Myb26: a MYB-like protein of pea flowers with affinity for promoters ofphenylpropanoid genes," Plant J. (1997) 12:6:1273-1284.

Urao et al., "An *Arabidopsis* myb Homolog Is Induced by Dehydration Stress and Its Gene Product Binds to the Conserved MYB Recognition Sequence," Plant Cell (1993) 5:1529-1539.

van Heiden et al., "A web site for the computational analysis of yeast regulatory sequences." Yeast (2000) 16:177-187.

Vander Mijnsbrugge et al., "Phenylcoumaran benzylic ether reductase, a prominent poplar xylem protein, is strongly associated with phenylpropanoid biosynthesis in lignifying cells," Planta (2000) 211:502-509.

Vasil et al., "Cell Culture and Somatic Cell Genetics, Volume 1 Laboratory Procedures and Their Applications," Academic Press (1984)—BOOK.

Vasil et al., "Cell Culture and Somatic Cell Genetics, Volume 2 Cell Growth, Nutrition, Cytodifferentiation, and Ctyopreservation," Academic Press (1985)—BOOK.

Vignols et al., "The brown midrib3 (bm3) Mutation in Maize Occures in the Gene Encoding Caffeic Acid O-Methyltransferase," Plant Cell (1995) 7:407-416.

Voo et al., "4-Coumarate:Coenzyme A Ligase from Loblolly Pine Xylem (Isolation, Characterization, and Complementary DNA Cloning)," Plant Physiol. (1995) 108:85-97.

Wait et al., "Controlling growth and chemical composition of samplings by iteratively matching nutrient sypply to demand: A bootstrap fertilization technique," Tree Physiol. (1996) 16:359-365.

Walter et al., "Cinnamyl-alcohol dehydrogenase, a molecular marker specific for lignin synthesis: cDNA cloning and mRNA induction by fungal elicitor," Proc. Natl. Acad. Sci. USA, (1988) 85:5546-5550.

Wan et al., "Generation of Large Numbers of Independently Transformed Fertile Barley Plants," Plant Physiol. (1994) 104:37-48.

Wang et al., "Overexpression of rice WRKY89 enhances ultraviolet B tolerance and disease resistance in rice plants," Plant Mol. Biol. (2007) 65:799-815.

Weigel et al., "The ABC's of Floral Homeotic Genes," Cell (1994) 78:203-209.

Weissbach and Weissbach, Methods for Plant Molecular Biology, Academic Press (1988)—BOOK.

Weisshaar et al., "Phenylpropanoid biosynthesis and its regulation," Current Opinion in Plant Biol. (1998) 1:251-257.

Wetmur et al., "Kinetics of Renaturation of DNA." J. Mol. Biol. (1968) 31:349-370.

Whetten et al., "Recent Advances in Understanding Lignin Biosynthesis," Annual Rev. Plant Physiology & Plant Mol. Biol. (1998) 49:585-609.

Whetten et al., "Genetic Engineering of Wood," Forest Ecol. Manage (1991) 43:301-316.

Whitelam et al., "Antibody Expression in Transgenic Plants," Trends in Plant Sci. (1996) 1:8:268-272.

Winkel-Shirley B., "Evidence for enzyme complexes in the phenylpropanoid and flavonoid pathways," Physiol. Plant. (1999) 107:142-149.

Winter et al., "Making Antibodies by Phage Display Technology," Annu. Rev. Immunol. (1994) 12:433-455.

Yalpani et al., "Pathway of salicylic acid biosynthesis in healthy and virus-inoculated tobacco," Plant Plysiol. (1993) 103:315-321.

Yang et al., A Calmodulin-binding/CGCG Box DNA-binding Protein Family Involved in Multiple Signaling Pathways in Plants, J. Biological Chem. (2002) 277:45049-45058.

Ye, Z-H. et al., "Differential expression of two O-methyltransferases in lignin biosynthesis in *Zinnia*," Plant Physiol. (1995) 108:459-467.

Ye et al., "An Alternative Methylation Pathway in Lignin Biosynthesis in *Zinnia*," Plant Cell (1994) 6:1427-1439.

Zhang et al., "Transgenic Rice Plants Produced by Electroporation-Mediated Plasmid Uptake into Protoplasts," Plant Cell Reports (1988) 7:379-384.

Zhang et al., "Molecular Cloning of 4-Coumarate:Coenzyme A Ligase in Loblolly Pine and the Roles of This Enzyme in the Biosynthesis of Lignin in Compression Wood," Plant Physiol. (1997) 113:65-74.

Zhou et al., "Stably Transformed Callus of Wheat by Electroporation-Induced Direct Gene Transfer," Plant Cell Reports (1993) 12:612-616.

U.S. Office Action (Oct. 3, 2006)—U.S. Appl. No. 10/769,350—28 pgs.

U.S. Office Action (Jan. 7, 1998)—U.S. Appl. No. 08/757,576—11 pgs.

Lindroth et al., "Responses of deciduous trees to elevated atmospheric CO2: productivity, phytochemistry and insect performance," Ecology (1993) 74:763-777.

Lloyd et al., "Commercially-Feasible Micropropagation of Mountain Laurel, *Kalmia latifolia*, by Use of Shoot-Tip Culture," Proc. Int. Plant Prop. Soc. (1980) 30:421-437.

Loake et al., "Combination of H-Box [CCTACC(N)7CT] and G-Box (CACGTG) cis Elements is Necessary for Feed-Forward Stimulation of a Chalcone Synthase Promoter by the Phenylpropanoid-Pathway Intermediate P-Coumaric Acid," Proc. Natl. Acad. Sci. (1992) 89:9230-9234.

Logemann et al., "Modes of expression and common structural features of the complete phenylalanine ammonia-lyase gene family in parsley," PNAS USA (1995) 92:5905-5909.

Lois et al., "A phenylalanine ammonia-lyase gene from parsley: structure, regulation and identification of elicitor and light responsive cis-acting elements," EMBO J. (1989) 8:1641-1648.

Lu et al., "Distinct Roles of Cinnamate 4-hydroxylase Genes in *Populus*," Plant Cell Physiol. (2006) 47:7:905-914.

Ma et al., "Antibody Production and Engineering in Plants," Annals of NY Acad. Sciences (1996) 792:1:72-81.

Ma, et al., "Generation and Assembly of Secretory Antibodies in Plants," Science (1995) 268:716-719.

Maliga et al., "Methods in Plant Molecular Biology, A Laboratory Course Manual," CSHL Press (1995) 233-399.

Maniatis et al., "Amplification and Characterization of a β-Globin Gene Synthesized in Vitro," Cell (1976) 8:163-182.

Marcotte et al., "Abscisic Acid-Responsive Sequences from the Em Gene of Wheat," Plant Cell (1989) 1:969-976.

Martin et al., "MYB transcription factors in plants," Trends in Genetics (1997) 13:67-73.

Martin, C., "Transcription Factors and the Manipulation of Plant Traits," Current Opinion in Biotech. (1996) 7:130-138.

Mason et al., "Transgenic Plants as Vaccine Production Systems," Trends in Biotech. (1995) 1-9.

Matteucci, et al., "Synthesis of Deoxyoligonucleotides on a Polymer Support," J. Am. Chem. Soc. (1981) 103:3185-3191.

McCabe et al., "Stable Transformation of Soybean (*Glycine max*) by Particle Acceleration," Bio/Technology (1988) 5:923-926.

Medina et al., "Phytoreactors show promise in treating munitions contaminants," Soil and Groundwater Cleanup (Feb./Mar. 1998) pp. 19-24.

Meilan et al., "Poplar (*Populus* spp.)," Methods in Mol. Biol. 344:2:143-151.

Mellerowicz et al., "Unravelling cell wall formation in the woody dicot stem," Plant Mol. Biol. (2001) 47:239-274.

Messing, et al., "Plant Gene Structure," Genetic Engineering of Plants (1983) Plenum Press NY 211-227.

Mizutani et al., "Isolation of a cDNA and a Genomic Clone Encoding Cinnamate 4-Hydroxylase from *Arabidopsis* and Its Expression Manner in Planta," Plant Physiol. (1997) 113:755-763.

Jones et al. "Photoaffinity Labeling with 5-Azidoindole-3-Acetic Acid," Methods in Plant Biochemistry and Molecular Biology (1989) Chapter 10 pp. 115-157.

Murai, N. "Molecular Analysis of cis-Acting Transcriptional Regulatory Elements and Transcriptional Factors in the Bean Seed Storage Protein Phaseolin Gene," CRC Press (1997) 397-421.

Murray et al., "Codon Usage in Plant Genes," Nucl. Acids Res. (1989) 17:2:477-498.

Musha et al., "Distribution of syringyl and guaiacyl moieties in hardwoods as indicated by ultraviolet microscopy," Wood Science and Technology (1975) 9:45-58.

Nagau et al., "A transient increase of phenylalanine ammonia-lyase transcript in kinetin-treated tobacco cells," Biosci. Biotech. Biochem. (1994) 58:558-559.

Nagao et al., "Identification of protein binding DNA sequences in an auxin-regulated gene of soybean." Plant Mol. Biol. (1993) 21:1147-1162.

Needleman et al., "A general method applicable to the search for similarities in the amino acid sequence of two proteins," J. Mol. Biol. (1970) 48:443-453.

Neustaedter et al., "A novel parsley 4CLI cis-element is required for developmentally regulated expression and protein-DNA complex formation," Plant J. (1999) 18:1:77-88.

Ni et al., "Strength and Tissue Specificity of Chimeric Promoters Derived from the Octopine and Mannopiine Synthase Genes," Plant J. (1995) 7:4:661-676.

Nicholson et al., "Phenolic Compounds and Their Role in Disease Resistance," Ann. Rev. Phytopathol. (1992) 30:369-389.

Norberg et al., "Physical and chemical properties of the gelatinous layer in tension wood fibre of aspen (*Populus tremula* L.)," Holzforschung (1966) 20:174-178.

O'Brien et al., "Polychormatic Staining of Plant Cell Walls by Toluidine Blue O," Protoplasma (1964) 59:367-373.

Odell, et al., "Identification of DNA sequences required for activity of the cauliflower mosaic virus 35S promoter," Nature (1985) 313:810-812.

Ohashi-Ito et al., "Class III Homeodomain Leucine-Zipper Proteins Regulate Xylem Cell Differentiation," Plant Cell Physiol. (2005) 46:10:1646-1656.

Ohl et al., "Functional Properties of a Phenylalanine Ammonia-Lyase Promoter from *Arabidopsis*," Plant Cell (1990) 2:837-848.

Osakabe et al., "Coniferyl aldehyde 5-hydroxylation and methylation direct syringyl lignin biosynthesis in angiosperms," Proc. Natl. Acad. Sci. (1999) 96:8955-8960.

Osakabe et al., "Characterization of the structure and determination of mRNA levels of phenylalanine ammonia-lyase gene family from *Populus kitakamiensis*," Plant Mol. Biol. (1995) 28:1133-1141.

Osakabe et al., "Immunocytochemical localization of phenylalanine ammonia-lyase in tissue of *Populus kitakamiensis*," Planta (1996) 200:13-19.

Osakabe et al., "Structure and tissue-specific expression of genes for phenylalanine ammonia-lyase from a hybrid aspen, *Populus kitakamiensis*," Plant Sci. (1995a) 105:217-226.

Parsons et al., "Systemic accumulation of specific mRNAs in response to wounding in poplar trees," PNAS USA (1989) 86:7895-7899.

Parvathi et al., "Substrate preferences of O⁻ methyltransferases in alfalfa suggest new pathways for 3-0-methylation of monolignols," Plant J. (2001) 25:2:193-202.

Pearl et al., "The Structures of Salicortin and Tremulacin," Phytochemistry (1971) 10:3161-3166.

Pearson et al., "Improved Tools for Biological Sequence Comparison," Proc. Natl. Acad. Sci. (1988) 85:2444-2448.

Pilate et al., "Tension wood as a model for functional genomics of wood formation," New Phytologist (2004) 164:63-72.

Pillonel et al., "Involvement of cinnamyl-alcohol dehydrogenase in the control of lignin formation in *Sorghum bicolor* L. Moench," Planta (1991) 185:538-544.

Pizzi, A., "Condensed Tannins for Adhesives," Ind. Eng. Chem. Prod. Res. Dev. (1982) 21:359-369.

Porter et al., "The conversion of procyanidins and prodelphinidins to cyanidin and delphinidin," Phytochem. (1986) 25:1:223-230.

Potrykus, I. "Gene Transfer to Plants: Assessment of Published Approaches and Results," Annu. Rev. Plant Physiol. Plant Mol. Biol. (1991) 42:205-225.

Poulsen et al., "Dissection of 5' Upstream Sequences for Selective Expression of the *Nicotiana plumbaginifoia* rbcS-8B Gene," Mol. Gen. Genet. (1988) 214:16-23.

Pouwels D.S.., Cloning Vectors, A Laboratory Manual (1985)—BOOK.

Pouwels et al., Cloning Vectors: A Laboratory Manual Supplementary Update 1987—BOOK.

Prestridge, "Signal Scan: A Computer Program that Scans DNA Sequences for Eukaryotic Transcriptional Elements," Cabios (1991) 7:2:203-206.

Raes et al., "Genome-Wide Characterization of the Lignification Toolbox in *Arabidopsis*," Plant Physiol. (2003) 133:1051-1071.

Rajinikanth et al., "The glycine decarboxylase complex multienzyme family in *Populus*," J. Exper. Bot. (2007) 58:7:1761-1770.

Rasmussen et al., "Transgene-mediated and elicitor-induced perturbation of metabolic channeling at the entry point into the phenylpropanoid pathway," Plant Cell (1999) 11:1537-1551.

Reed et al., "Effects of 76 Hz electromagnetic fields on forest ecosystems in northern Michigan: tree growth," Int. J. Biometeorol. (1993) 37:229-234.

Reeve, R.M., "Histological tests for polyphenols in plant tissues," Stain Tech. (1951) 26:91-96.

Reyes et al., "The GATA Family of Transcription Factors in *Arabidopsis* and Rice," Plant Physiol. (2004) 134:1718-1732.

Rhodes, et al., "Genetically Transformed Maize Plants from Protoplasts," Science (1988) 240:204-206.

Ribnicky et al., "Intermediates of salicylic acid biosynthesis in tobacco," Plant Physiol. (1998) 118:565-572.

Rivera et al., "Phytotreatment of TNT-Contaminated Groundwater," J. Soil Contamination (1998) 7:4:511-529.

Rogers et al., "Improved Vectors for Plant Transformation: Expression Cassette Vectors and New Selectable Markers," Methods in Enzymology (1987) pp. 253-277.

Rosahl et al., "Expression of a Tuber-Specific Storage Protein in Transgenic Tobacco Plants: Demonstration of an Esterase Activity," EMBO J. (1987) 6:5:1155-1159.

Rose et al., "The tomato I-box binding factor LeMYBI is a member of a novel class of myb-like proteins," Plant J. (1999) 20:6:641-652.

Rugh et al., "Development of transgenic yellow poplar for mercury phytoremediation," Nature Biotech. (1998) 16:925-928.

Rushton et al., "Aleurone nuclear proteins bind to similar elements in the promoter regions of two gibberellin-regulated alpha-amylase genes," Plant Mol Biol. (1992) 19: 891-901.

Rushton et al., "Interaction of elicitor-induced DNA-binding proteins with elicitor response elements in the promoters of parsley PR1 genes," EMBO J. (1996) 15:20:5690-5700.

Sablowski et al., "A flower-specific Myb protein activates transcription of phenylpropanoid biosynthetic genes," EMBO J. (1994) 13:1:128-137.

Sachs A.B., "Messenger RNA Degradation in Eukaryotes," Cell (1993) 74:413-421.

Saka et al., "Localization of Lignins in Wood Cell Walls," Biosynthesis and Biodegradation of Wood Components (1985) pp. 51-62.

Sambrook et al., "Hybridization of Radiolabeled Probes to Immobilized Nucleic Acids," Analysis & Cloning of Eukaryotic Genomic DNA (1989) 9.47-9.62—BOOK.

Sambrook et al., Molecular Cloning: A Laboratory Manual, 2nd Edition, Cold Spring Harbor Laboratory Press, Cold Spring Harbor, NY (1989)—BOOK.

Sanders et al., "Communicating with Calcium," Plant Cell (1999) 11:691-706.

Sanders et al., "Calcium at the Crossroads of Signaling," Plant Cell (2002) pp. S401-S417.

Sarma et al., "Differential expression and properties of phenylalanine ammonia-lyase isoforms in tomato leaves," Phytochem. (1998) 49:2233-2243.

Schaffner, et al., "Maize rbcS Promoter Activity Depends on Sequence Elements not Found in Dicot rbcS Promoters," Plant Cell (1991) 3:997-1012.

Schernthaner et al., "Endosperm-Specific Activity of a Zein Gene Promoter in Transgenic Tobacco Plants," EMBO J. (1988) 7:5:1249-1255.

Sethi et al., "Studies on Wheat Protoplasts—A Rapid and Large-Scale Isolation Method and Cell Wall Regeneration in Cultures," Jap. J. Crop. Sci. (1983) 52:2:158-167.

Sharp et al., "Chapter 10—Development of Highly Specific Antibodies to Alachlor by Use of a Carboxy-Alachlor Protein Conjugate," American Chem. Soc. Symposium Series Pesticide Residues and Food Safety, (1991) 87-95.

Sheen J., "Molecular Mechanisms Underlying the Differential Expression of Maize Pyruvate, Orthophosphate Dikinase Genes," Plant Cell (1991) 3:225-245.

Shen et al., "Functional Dissection of an Abscisic Acid (ABA)-Inducible Gene Reveals Two Independent ABA-Responsive Complexes Each Containing a G-Box and a Novel cis-Acting Element," Plant Cell (1995) 7:295-307.

Shen et al., "Modular Nature of Abscisic Acid (ABA) Response Complexes: Composite Promoter Units That are Necessary and Sufficient for ABA Induction of Gene Expression in Barley," Plant Cell (1996) 8:1107-1119.

Shufflebottom et al., "Transcription of two members of a gene family encoding phenylalanine ammonia-lyase leads to remarkably different cell specificities and induction patters," Plant J. (1993) 3:6:835-845.

Siebertz et al., "cis-Analysis of the Wound-Inducible Promoter wun1 in Transgenic Tobacco Plants and Histochemical Localization of Its Expression," Plant Cell (1989) 1:961-968.

Simpson et al., "Light-Inducible and Tissue-Specific Expression of a Chimaeric Gene Under Control of the 5'-Flanking Sequence of a Pea Chlorophyll a/b-Binding Protein Gene," EMBO J. (1985) 4:11:2723-2729.

Skriver et al., "Cis-acting DNA elements responsive to gibberellin and its antagonist abscisic acid," Proc. Natl. Acad. Sci. (1991) 88:7266-7270.

Smith T.F. et al., "Comparison of Biosequences," Adv. in Applied Math. (1981) 2:482-489.

Somers et al., "Fertile, Transgenic Oat Plants," Biotechnology (1992) 10:1589-1594.

Sterky et al., "A *Populus* EST resource for plant functional genomics," Proc. Natl. Acad. Sci. (2004) 101:38:13951-13956.

Stitt et al., "The interaction between elevated carbon dioxide and nitrogen nutrition: the physiological and molecular backgrounds," Plant, Cell and Environment (1999) 22:583-621.

Stitt et al., "Steps towards an integrated view of nitrogen metabolism," J. Exp. Botany (2002) 53:70:959-970.

Strauss et al., "Ten lessons from 15 years of transgenic *Populus* research," Forestry (2004) 77:5:455-463.

Strittmatter et al., "Artificial Combination of Two cis-Regulatory Elements Generates a Unique Pattern of Expression in Transgenic Plants," Proc. Natl. Acad. Sci. (1987) 84:8986-8990.

Subramaniam et al., "Structure, inhereitance, and expression of hybrid poplar (*Populus trichocarpa* x *Populus deltoides*) phenylalanine ammonia-lyase genes," Plant Physiol. (1993) 102:71-83.

Sweetlove et al., "Predictive metabolic engineering: a goal for systems biology," Plant Physiol. (2003) 132:420-425.

Szerszen et al., "iaglu, a Gene from *Zea mays* Involved in Conjugation of Growth Hormone Indone-3-Acetic Acid," Science (1994) 265:1699-1701.

Tamagnone et al., ","The AmMYB308 and AmMYB330 Transcription Factors from Antirrhinum Regulate Phenylpropanoid and Lignin Biosynthesis in Transgenic Tobacco, Plant Cell (1998) 10:135-154.

Teakle et al., "Two forms of type IV zinc-finger motif and their kingdom-specific distribution between the flora, fauna and fungi," (1998) TIBS 23:100-102.

Terada et al., "Expression of CaMV35S-GUS Gene in Transgenic Rice Plants," Mol. Gen. Genet. (1990) 220:389-392.

Casas et al., "Transgenic Sorghum Plants via Microprojectile Bombardment," Proc. Natl. Acad. Sci. (1993) 90:11212-11216.

Chang et al., "A simple and efficient method for isolating RNA from pine trees," Plant Mol. Biol. Rep. (1993) 11:113-116.

Chappell et al., "Transcription of plant defence genes in response to UV light or fungal elicitor," Nature (1984) 311: 76-78.

Chapple et al., "An *Arabidopsis* Mutant Defective in the General Phenylpropanoid Pathway," Plant Cell (1992) 4:1413-1424.

Chen et al., "Cell-Specific and Conditional Expression of Caffeoyl-Coenzyme A-3-0-Methyltransferase in Poplar," Plant Physiol. (2000) 123: 853-867.

Chen et al., "Chemical syntheses of caffeoyl and 5¬OH coniferyl aldehydes and alcohols and determination of lignin O-methyltransferase activities in dicot and monocot species," Phytochem. (2001) 58:1035-1042.

Cheng et al., "Production of Fertile Transgenic Peanut (*Arachis hypogaea* L.) Plants Using *Agrobacteriium tumefaciens*," Plant Cell Reports (1996) 15:653-657.

Chiang et al., "Regulation of Lignin Biosynthesis in Transgenic Quaking Aspen (*Populus tremuloides*)," Biological Sciences Symposium, Minneapolis, MN Oct. 3-6, 1994 pp. 167-171.
Chiang et al., "Comparison of softwood and hardwood kraft pulping," Tappi J. (1988) 71:173-176.
Chinnusamy et al., "Molecular genetic perspectives on cross-talk and specificity in abiotic stress signalling in plants," J. Exp. Botany (2004) 55:225-236.
Christou et al., "Production of Transgenic Rice (*Oryza sativa* L) Plants from Agronomically Important *indica* and *japonica* Varieties via Electric Discharge Particle Acceleration of Exogenous DNA into Immature Zygotic Embryos," Bio/Technology (1991) 9:957-962.
Christou et al., "Stable Transformation of Soybean Callus by DNA-Coated Gold Particles," Plant Physiol. (1988) 87:671-674.
Church et al., "Genomic sequencing," Proc. Natl. Acad. Sci. (1994) 81:1991-1995.
Coleclough et al., "Use of Primer-Restriction-End Adapters in a Novel cDNA Cloning Strategy," Gene (1985) 34:305-314.
Comai et al., "Novel and Useful Properties of a Chimeric Plant Promoter Combining CaMV 35S and MAS Elements," Plant Molecular Biol. (1990) 15:373-381.
Coquoz et al., "The biosynthesis of salicyclic acid in potato plants," Plant Physiol. (1998) 117:1095-1101.
Coulson A., "High-Performance Searching of Biosequence Databases," Trends in Biotech. (1994) 12:76-80.
Cramer et al., "Phenylalanine ammonia-lyase gene organization and structure," Plant Mol. Biol. (1989) 12:367-383.
Crawford N.M., "Nitrate: Nutrient and Signal for Plant Growth," Plant Cell (1995) 7:859¬868.
Croy, R.R.D., "Plant Molecular Biology," Dept. Biological Sciences, Univ. Durhan, BIOS Scientific Publishers (1993)—BOOK.
Cunningham, et al., "Phytoremediation: Plant-based remediation of contaminated soils and sediments," Bioremediation: Science and Applications. Soil Science Society of America, Special Publication (1995) 43:145-156.
Current Protocols in Molecular Biology, John Wiley & Sons, NY (1989) 6.3.1-6.3.6—BOOK.
Current Protocols in Molecular Biology, John Wiley & Sons, NY vol. 1 (1987-1994)—BOOK.
Dalkin et al., Stress Responses in Alfalfa (*Medicago sativa* L.) Plant Physiol. (1990) 92:440-446.
Davidson, Gene Activity in Early Development, 2nd edition, Academic Press, New York (1976)—BOOK.
Davis et al., "A family of wound-induced genes in *Populus* shares common features with genes encoding vegatative storage proteins," Plant Mol. Biol. (1993) 23:135-143.
Davis et al., "Assimilate movement dictates remote sites of wound-induced gene expression in poplar leaves," PNAS USA (1991) 88:2393-2396.
De Block M., "Factors Influencing the Tissue Culture and the *Agrobacterium tumefaciens*—Mediated Transformation of Hybrid Aspen and Poplar Clones," Plant Physiol. (1990) 93:1110-1116.
Dean et al., "Biotechnological Modification of Lignin Structure and Composition in Forest Trees," Holzforschung (1992) 46:135-147.
Dekeyser, et al., "Transient Gene Expression in Intact and Organized Rice Tissues," Plant Cell (1990) 2:591-602.
Della-Cioppa et al., "Targeting a Herbicide-Resistant Enzyme from *Escherichia coli* to Chloroplasts of Higher Plants," Bio/Technology (1987) 5:579-584.
Dixon et al., "Stress-Induced Phenylpropanoid Metabolism," Plant Cell (1995) 7:1085-1097.
Donald et al., "Mutation of either G box or I box sequences profoundly affects expression from the *Arabidopsis* rbcS-I A promoter," EMBO J. (1990) 9:6:1717-1726.
Donaldson L.A., "Lignification and lignin topochemistry—an ultrastructural view," Phytochem. (2001) 57:859-873.
Douglas C.J. "Phenylpropanoid metabolism and lignin biosynthesis: from weeds to trees," Trends in Plant Sci. (1996) 1:6:171-178.
Edwards et al., "A simple and rapid method for the preparation of plant genomic DNA for PCR analysis," Nucleic Acids Res. (1991) 19:6:1349.
Efstratiadis et al., "Enzymatic in vitro Synthesis of Globin Genes," Cell (1976) 7:279-288.

Ehlting et al., Three 4-coumarate:coenzyme A ligases in *Arabidopsis thaliana* represent two evolutionarily divergent classes in angiosperms. Plant J. (1999) 19:9-20.
Ehness et al., "Glucoase and stress independently regulate source and sink metabolism and defense mechanisms via signal transduction pathways involving protein phosphorylation," Plant Cell (1997) 9:1825-1841.
Ellis et al., "The ocs element: a 16 base pair palindrome essential for activity of the octopine synthase enhancer," EMBO J. (1987) 6:11:3203-3208.
Eulgem et al., "The WRKY superfamily of plant transcription factors," Trends in Plant Sci. (2000) 5:5:199-206.
Eulgem et al., "Early nuclear events in plant defence signalling: rapid gene activation by WRKY transcription factors," EMBO J. (1999) 18:17:4689-4699.
Fergus et al., "The Location of Guaiacyl and Syringyl Lignins in Birch Xylem Tissue," Holzforschung (1970) 24:113-117.
Feucht et al., "Flavan-3-ols in trichomes, pistils and phelloderm of some tree species," Ann. Bot. (1990) 65:225-230.
Feuillet et al., "Tissue- and cell-specific expression of a cinnamyl alcohol dehydrogenase promoter in transgenic poplar plants," Plant Mol. Biol. (1995) 27:651-667.
Finkelstein et al., "The *Arabidopsis* Abscisic Acid Response Gene ABI5 Encodes a Basic Leucine Zipper Transcription Factor," Plant Cell (2000) 12:599-609.
Fluhr et al., "Organ-Specific and Light-Induced Expression of Plant Genes," Science (1986) 232:1106-1112.
Fraley et al., "Expression of Bacterial Genes in Plant Cells," Proc. Natl. Acad. Sci. (1983) 80:4803-4807.
Frohman, et al., "Rapid production of full-length cDNAs from rare transcripts: Amplification using a single gene-specific oligonucleotide primer," Proc. Natl. Acad. Sci. (1988) 85:8998-9002.
Holsters et al., "Transfection and transformation of *Agrobacterium tumefaciens*," Mol. Gen. Genet. (1978) 163:181-187.
Hoogenboom, H.R., "Designing and Optimizing Library Selection Strategies for Generating High-Affinity Antibodies," Tibtech (1997) 15:62-70.
Horn et al., "Transgenic Plants of Orchardgrass (*Dactylis glomerate* L.) from Protoplasts," Plant Cell Rep. (1988) 7:469-472.
Howels et al., "Overexpression of L-phenylalanine ammonia-lyase in transgenic tobacco plants reveals control points for flux into phenylpropanoid biosyntehsis," Plant Phys. (1996) 112:1617-1624.
Hu, W.-J., "Isolation and Characterization of P-Coumarate:Coenzyme a Ligase cDNAS and Genes from Quaking Aspen," (1997) Dissertation.
Hu et al., "Compartmentalized expression of two structurally and functionally distinct 4-coumarate:CoA ligase genes in aspen (*Populus tremuloids*)," PNAS USA (1998) 95:5407-5412.
Hu et al., "Repression of lignin biosynthesis promotes cellulose accumulation and growth in transgenic trees," Nature Biotech. (1999) 17:808-812.
Iiyama et al., "An improved acetyl bromide procedure for determining lignin in woods and wood pulps," Wood Sci. Technol. (1988) 22:271-280.
Innis et al., PCR Protocols: A Guide to Methods and Applications, Academic Press, San Diego (1990)—BOOK.
International Search Report and Written Opinion for Application No. PCT/US2009/041956 dated Oct. 7, 2009 (15 pgs.).
Jefferson, R.A.., "Assaying Chimeric Genes in Plants: The GUS Gene Fusion System," Plant Mol. Biol. (1987) 5:387-405.
Jefferson et al., "GUS fusions: Beta-glucuronidase as a sensitive and versatile gene fusion marker in higher plants," EMBO J. (1987) 6:13:3901-3907.
Jin et al., "Transcriptional repression by AtMYB4 controls production of UV¬ protecting sunscreens in *Arabidopsis*," The EMBO J. (2000) 19:22:6150-6161.
Johnson et al., "Eukaryotic Transcriptional Regulatory Proteins," Annu. Rev. Biochem. (1989) 58:799-839.
Jones, D.H., "Phenylalanine ammonia-lyase: regulation of its induction, and its role in plant development," Phytochem. (1984) 23:1349-1359.
Joseleau et al., "Study of Lignification by Noninvasive Techniques in Growing Maize Internodes," Plant Physiol. (1997) 114:1123-1133.

Joshi et al., "Application of modified differential display technique for cloning and sequencing of the 3' region from three putative members of wheat HSP70 gene family," Plant Mol. Biol. (1996) 30:641-646.

Jouanin et al., "Lignification in Transgenic Poplars with Extremely Reduced Caffeic Acid O-Methyltransferase Activity," Plant Physiol. (2000) 123: 1363-1373.

Jourez et al., "Anatomical characteristics of tension wood and opposite wood in young inclined stems of poplar (*Populus euramericana* cv 'Ghoy')," IAWA J. (2001) 22:2:133-157.

Julkunen-Tiitto et al., "Increased CO2 and nutrient status changes affect phytomass and the production of plant defensive secondary chemicals in *Salix myrsinifolia* (Salisb.)," Oecologia (1993) 95:495-498.

Kanehisa, M., "Use of Statistical Criteria for Screening Potential Homologies in Nucleic Acid Sequences," Nucl. Acids Res. (1984) 12:1:203-213.

Kao et al., "Differential expression of two distinct phenylalanine ammonia-lyase genes in condensed tannin-accumulating and lignifying cells of quaking aspen," Plant Physiol. (2002) 130:796-807.

Khoury et al., "Enhancer Elements," Cell (1983) 33:313-314.

Kim et al., "Isolation of a novel class of bZIP transcription factors that interact with ABA-responsive and embryo specification elements in the Dc3 promoter using a modified yeast one-hybrid system," Plant J. (1997) 11:6:1237-1251.

Kleiner, et al., "Partitioning of 14C-labeled photosynthate to allelochemicals and primary metabolites in source and sink leaves of aspen: evidence for secondary metabolite turnover," Oecologia (1999) 119:408-418.

Knight et al., "Cold Calcium Signaling in *Arabidopsis* Involves Two Cellular Pools and a Change in Calcium Signature after Acclimation," Plant Cell (1996) 8:489-503.

Knight et al., "Calcium Signaling in *Arabidopsis thaliana* Responding to Drought and Salinity," Plant J. (1997) 12:5:1067-1078.

Knogge et al., "Tissue-distribution of secondary phenolic biosyntehsis in developing primary leaves of *Avena sativa*," L. Planta (1986) 167:196-205.

Ko et al., "Plant Body Weight-Induced Secondary Growth in *Arabidopsis* and Its Transcription Phenotype Revealed by Whole ¬ Transcriptome Profiling," Plant Physiol. (2004) 135:1069-1083.

Kohler et al., "Continuous Cultures of Fused Cells Secreting Antibody of Predefined Specificity," Nature (1975) 256:495-497.

Koncz et al., "The promoter of TL-DNA gene 5 controls the tissue-specific expression of chimeric gene carried by a novel type of *Agrobacterium* binary vector," Mol. Gen. Genet. (1986) 204:383-396.

Koziel et al., "Field Performance of Elite Transgenic Maize Plants Expressing an Insecticidal Protein Derived from *Bacillus thuringiensis*," Bio/Technology (1993) 11:194-200.

Krawinkel et al., "Rapid Synthesis of cDNA for Cloning into Lambda Vectors," Nucl. Acids Res. (1986) 14(4):1913.

Kuhlemeier et al., "The Pea rbcS-3A Promoter Mediates Light Responsiveness but not Organ Specificity," Plant Cell (1989) 1:471-478.

Kumar et al., "The phenylalanine ammonia-lyase gene family in raspberry. Structure, expression, and evolution," Plant Physiol. (2001) 127:230-239.

Lacombe et al., "Characterization of cis-elements required for vascular expression of the Cinnamoyl CoA Reductase gene and for protein-DNA complex formation," Plant J. (2000) 23:663-676.

Lam et al., "ASF-2: A Factor That Binds to the Cauliflower Mosaic Virus 35S Promoter and a Conserved GATA Motifin Cab Promoters," Plant Cell (1989) 1:1147-1156.

Land et al., "5'-Terminal Sequences of Eucaryotic mRNA Can be Cloned with High Efficiency," Nucl. Acids Res. (1981) 9:10:2251-2266.

Lapierre et al., "Structural Alterations of Lignins in Transgenic Poplars with Depressed Cinnamyl Alcohol Dehydrogenase or Caffeic Acid O-Methyltransferase Activity Have an Opposite Impact on the Efficiency of Industrial Kraft Pulping," Plant Physiol. (1999) 119: 153-163.

Lauvergeat et al., "Two cinnamoyl-CoA reductase (CCR) genes from *Arabidopsis thaliana* are differentially expressed during development and in response to infection with pathogenic bacteria," Phytochemistry (2001) 57:1187-1195.

Lauvergeat et al., "The vascular expression pattern directed by the *Eucalyptus gunnii* cinnamyl alcohol dehydrogenase EgCAD2 promoter is conserved among woody and herbaceous plant species," Plant Mol. Biol. (2002) 50:497-509.

Lawton et al., "Transcriptional activation of plant defense genes by fungal elicitor, wounding, and infection," Mol. Cell. Biol. (1987) 7:1:335-341.

Lee et al., The *Arabidopsis thaliana* 4-coumarate:CoA ligase (4CL) gene: stress and developmentally regulated expression and nucleotide sequence of its cDNA. Plant Mol. Biol. (1995) 28: 871-884.

Lee et al., "Two divergent members of a tobacco 4-coumarate: coenzyme A ligase (4CL) gene family," Plant Physiol. (1996) 112:193-205.

Lewis et al., "Lignin: Occurrence, Biogenesis and Biodegradation," Annu. Rev. Plant Physiol. Plant Mol. Biol. (1990) 41:455-496.

Leyva et al., "cis-Element Combinations Determine Phenylalanine Ammonia-Lyase Gene Tissue-Specific Expression Patterns," Plant Cell (1992) 4:263-271.

Li et al., "5-Hydroxy-coniferyl aldehyde modulates enzymatic methylation for syringyl monolignol formation: a new view of monolignol biosynthesis in angiosperms," J. Biol. Chem. (2000) 275:6537-6545.

Liang et al., "Distribution and cloning of eukaryotic mRNAs by means of diffferential display: refinements and optimization," Nucl. Acids Res. (1993) 21:14:3269-3275.

Liang et al., "Differential regulation of phenylalanine ammonia-lyase genes during plant development and by environmental cues," J. Biol. Chem. (1989) 264:14486-14492.

Lindroth et al., "Diversity, redundancy, and multiplicity in chemical defense systems of aspen," Phytochemical diversity and redundancy in ecological interactions, Romeo et al., eds., Plenum Press, New York (1996) 25-51.

Fromm et al., "An Octopine Synthase Enhancer Element Directs Tissue-Specific Expression and Binds ASF-1, a Factor from Tobacco Nuclear Extracts," Plant Cell (1989) 1:977-984.

Fromm et al., "Inheritance and Expression of Chimeric Genes in the Progeny of Transgenic Maize Plants," Bio. Technology (1990) 8:833-839.

Funaoka et al., "Nucleus Exchange Reaction," Mehods in Lignin Chemistry (1992) pp. 369-384.

Gardner R.O., "Vanillin-hydrochloric acid as a histochemical test for tannin," Stain Tech. (1975) 50:315-317.

Ge et al., "A full length cDNA encoding trans-cinnamate 4-hydroxylase from developing xylem of *Populus tremuloidesss* (Accession No. U47293) (PGR96-075)," Plant Physiol. (1996) 112:861.

Gelvin et al., Plant Molecular Biology Manual, Kluwer Academic Publishers (1988-1993)—BOOK.

Gelvin, S.B., "Molecular Genetics of T-DNA Transfer from *Agrobacterium* to Plants," Transgenic Plants (1993) 1:49-87.

Gibson et al., "Ribozymes, Their Functions and Strategies for Their Use," Molecular BioTechnology (1997) 7:125-137.

Gilmartin et al., "Molecular Light Switches for Plant Genes," Plant Cell (1990) 2:369-378.

Gordon-Kamm et al., "Transformation of Maize Cells and Regeneration of Fertile Transgenic Plants," Plant Cell (1990) 2:603-618.

Goujon et al., "A new *Arabidopsis thaliana* mutant deficient in the expression of O-methyltransferase impacts lignins and sinapoyl esters," Plant Mol. Biol. (2003) 51:973-989.

Grand, C., "Ferulic acid 5-hydroxylase: a new cytochrome P-450-dependent enzyme from higher plant microsomes involved in lignin synthesis", Fed. Europ. Biochem. Soci. (1984) 169:1—BOOK.

Grand et al., "Isoenzymes of hydroxycinnamate: CoA ligase from poplar stems properties and tissue distribution," Planta (1983) 158:225-229.

Gray-Mitsumune et al., "Developmentally regulated patterns of expression directed by poplar PAL promoters in transgenic tobacco and poplar," Plant Mol. Biol. (1999) 39:657-669.

Green P.J., "Control of mRNA Stability in Higher Plants," Plant Physiol. (1993) 102:1065-1070.

Grimmig et al., "Structure of the parsley caffeoyl-CoA O¬ methyltransferase gene, harbouring a novel elicitor responsive cis-acting element," Plant Mol. Biol. (1997) 33:323-341.

Grotewold et al., "The myb-Homologous P gene Controls Phlobaphene Pigmentation in Maize Floral Organs by Directly Activating a Flavonoid Biosynthetic Gene Subset," Cell (1994) 76:543-553.

Gruss et al., "Simian Virus 40 Tandem Repeated Sequences as an Element of the Early Promoter," Proc. Natl. Acad. Sci. (1981) 78:2:943-947.

Gubler et al., "Gibberellin-Regulated Expression of a myb Gene in Barley Aleurone Cells: Evidence for Myb Transactivation of a High-pI [alpha]-Amylase Gene Promoter," Plant Cell (1995) 7:1879-1891.

Guo et al., "Downregulation of Caffeic Acid 3-0-Methyltransferase and Caffeoyl CoA 3-0-Methyltransferase in Transgenic Alfalfa: Impacts on Lignin Structure and Implications for the Biosynthesis of G and S Lignin," Plant Cell.(2001) 13:73-88.

Hahlbrock et al., "Physiology and molecular biology of phenylpropanoid metabolism," Ann. Rev. Plant Physiol. Plant Mol. Biol. (1989) 40:347-369.

Hahlbrock et al., "Oligopeptide Elicitor-Mediated Defense Gene Activation in Cultured Parsley Cells," Proc. Natl. Acad. Sci. (1985) 92:4150-4157.

Hahlbrock et al., "Enzymic controls in the biosynthesis of lignin and flavonoids," Ann. Rev. Plant Physiol. (1979) 30:105-130.

Halpin et al., "Manipulation of lignin quality by downregulation of cinnamyl alcohol dehydrogenase," Plant J. (1994) 6:3:339-350.

Hamberger et al., "The 4-coumarate:CoA ligase gene family in *Arabidopsis thaliana* comprises one rare, sinapate-activating and three commonly occurring isoenzymes," Proc. Nat. Acad. Sci. (2004) 101:7:2209-2214.

Hamberger et al., "Genome-wide analyses of phenylpropanoid-related genes in *Populus trichocarpa, Arabidopsis thalliana* and *Oryza sativa*: the *Populus* lignin toolbox and conservation and diversification of Angiosperm gene families," Can. J. Bot. (2007) 85:1182-1201.

Hamilton et al., "Antisense gene that inhibits synthesis of the hormone ethylene in transgenic plants," Nature (1990) 346:284-287.

Han et al., "λgt22 An Improved Vector for the Directional Cloning of Full-Length cDNA," Nucl. Acid Res. (1987) 15:15:6304.

Han et al., "An *Agrobacterium tumefaciens* transformation protocol effective on a variety of cottonwood hybrids (genus *Populus*)," Plant Cell Report (2000) 19:315-320.

Harding et al., "Functional genomics analysis of foliar condensed tannin and phenolic glycoside regulation in natural cottonwood hybrids," Tree Physiol. (2005) 25:1475-1486.

Harding et al., "Differential substrate inhibition couples kinetically distinct 4-coumarate: CoA ligases with spatially distinct metabolic roles in quaking aspen," Plant Physiol. (2002) 128:428-438.

Harlow et al., "Antibodies, A Laboratory Manual," (1988)—BOOK.

Harmer et al., "Orchestrated Transcription of Key Pathways in *Arabidopsis* by the Circadian Clock," Science (2000) 290:2110-2113.

Hatton et al., "Two classes of cis sequences contribute to tissue-specific expression of a PAL2 promoter in transgenic tobacco," Plant J. (1995) 7:859-876.

Hauffe et al., "Combinatorial interactions between positive and negative cis-acting elements control spatial patterns of 4CL-I expression in transgenic tobacco," Plant J. (1993) 4:2:235-253.

Hauffe et al., "A Parsley 4CL-I Promoter Fragment Specifies Complex Expression Patterns in Transgenic Tobacco," Plant Cell (1991) 3:435-443.

Hawkins et al., "Cinnamyl Alcohol Dehydrogenase: Identification of New Sites of Promoter Activity in Transgenic Poplar," Plant Physiol. (1997) 113:321-325.

Hayakawa et al., "Molecular cloning and tissue-specific expression of two genes that encode caffeic acid O-methyltransferases from *Populus kitakamiensis*," Plant Sci. (1996) 13:157-165.

Hayakawa et al., "*Populus kitakamiensis (P. sieboldii* X *P. grandidentata*) homt1 gene for caffeic acid O-methyltransferase, complete cds (exon1-4)," EMBL Database accession No. D49710, (1995) Abstract.

Haymes et al., Nucleic Acid Hybridization, A Practical Approach, IRL Press, Washington DC (1985)—BOOK.

Heinemeyer et al., "Expanding the TRANSFAC Database Towards an Expert System of Regulatory Molecular Mechanisms," Nucl. Acids Res. (1999) 27:1:318-322.

Hemm et al., "AtMYB4: a transcription factor general in the battle against UV," Trends in Plant Science (2001) 6:135-136.

Hiatt et al., "Production of Antibodies in Transgenic Plants," Nature (1989) 342:2:76-78.

"Hibino et al., ""Increase of Cinnamaldehyde Groups in Lignin of Transgenic Tobacco Plants Carrying an Antisense Gene for Cinnamyl Alcohol Dehydrogenase," Biosci. Biotech. Biochem. (1995) 59:929-931.

Higo et al., "Plant Cis-Acting Regulatory DNA Elements (PLACE) Database: 1999," Nucl. Acids Res. (1999) 27:1:297-300.

Higuchi, T., "Biosynthesis of lignin, Biosynthesis and Biodegradation of Wood Components," Orlando FL: Academic Press (1985) pp. 141-160.

Higuchi et al., "A General Method for Cloning Eukaryotic Structural Gene Sequences," Proc. Natl. Acad. Sci. (1976) 73:9:3146-3150.

Higuchi T., Biochemistry and Molecular Biology of Wood (Springer Series in Wood Science). Springer-Verlag, Berlin—(1997) BOOK.

Ferreira et al., "Control of cell proliferation during plant development," Plant Mol. Biol. (1994) 26:1289-1303.

Hobo et al., "ACGT-containing abscisic acid reponse element (ABRE) and coupling element 3 (CE3) are functionally equivalent," Plant J. (1999) 19:679-689.

* cited by examiner

```
-473                                                          -414
TAAGTTCAGTAAATATAATCGGGTGAATATCTCATCATGTAATTAAATATCTTAATCTC
        YACT (- strand, YACT box)
             NGATT (- strand, ARR element)
                GTGA (+ strand, GTGA motif)
                   GATA (- strand, GATA box)
                            AATTAAA(AT rich)
                                 GATA (-, GATA box)
                                     NGATT (-, ARR)
```

```
         WT    AGTTCAGTAAATATAATCGGGTGAATATCTCATCA  (Positions 3-34
(inclusive) of SEQ ID NO. 1)
         Mut2  AGTTCAGTAAATATccTaGGGTGAATgctTCATCA  (SEQ ID NO:7)
         Mut3  AGTTCAGTAAATATccTaGGGTGAATATCTCATCA  (SEQ ID NO:8)
         Mut4  AGTTCAGTAAATATAATCGGGTGAATgctTCATCA  (SEQ ID NO:9)
         Mut5  AGTTCAGTAAATATAATCGGtcctATgctTCATCA  (SEQ ID NO:10)
         Mut6  AGTTCAGTAAATATccTacGtcctATgctTCATCA  (SEQ ID NO:11)
         Mut7  AGTTCttcAAATATccTacGtcctATgctTCATCA  (SEQ ID NO:12)
```

B

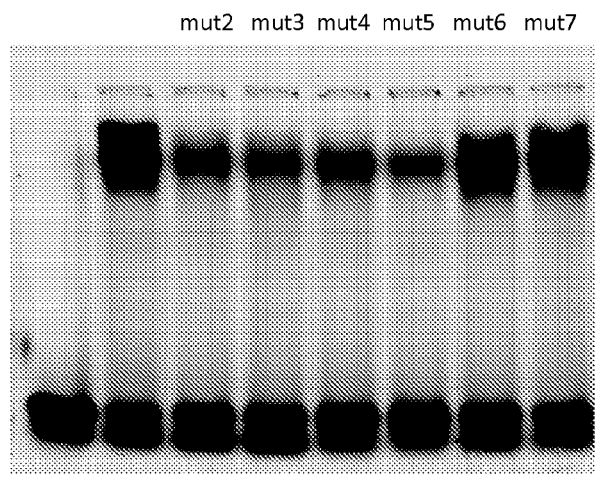

| | | mut2 | mut3 | mut4 | mut5 | mut6 | mut7 |

Comt1-471 probe    + + + + + + + +
xylem    − + + + + + + +
Mutant competitor    − − + + + + + +

```
WT-450      TGAATATCTCATCATGTAATTAAATATCTTAATC (Positions 24-
57 (inclusive)of SEQ ID NO: 1)
Mut 3       TGAATgcCTCATCATGTAAccAcATgcCTTAATC (SEQ ID NO:13)
Mut 4       TGAATgcCTCATCATGTAATTAAATgcCTTAATC (SEQ ID NO:14)
Mut 5       TGAATgcCTCATCATGTAAccAcATATCTTAATC (SEQ ID NO:15)
Mut 6       TGAATATCTCATCATGTAAccAcATATCTTAATC (SEQ ID NO:16)
Mut 7       TGAATATCTCATCATGTAATTAAATgcCTTAATC (SEQ ID NO:17)
Mut 8       TGAATgcCTCATCATGTAATTAAATATCTTAATC (SEQ ID NO:18)
Mut 9       TGccTgctTCATCATGTAATTAAATATCTTAATC (SEQ ID NO:19)
Mut 10      TGccTgctTCATCATGTAAccAtAgcTgTTAATC (SEQ ID NO:20)
Mut 11      TGccTgctTCtttcTGTAATTAAATATCTTAATC (SEQ ID NO:21)
Mut 12      TGccTgctTCATCATccttTTAAATATCTTAATC (SEQ ID NO:22)
```

B

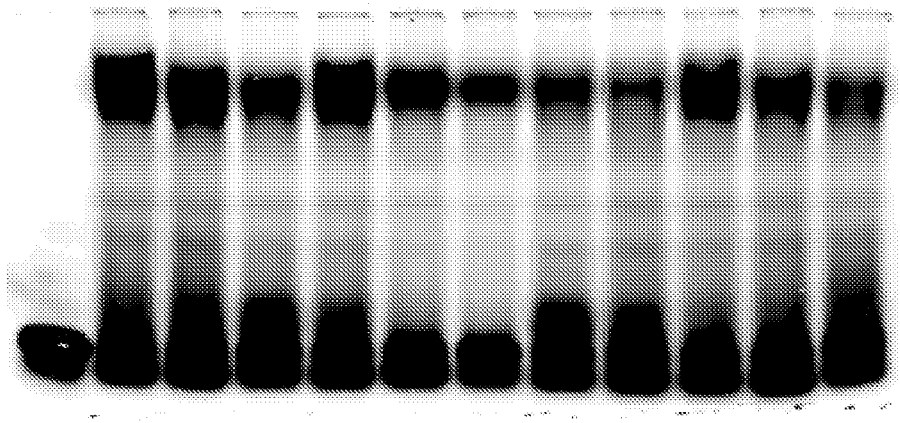

```
        WT -422  TTAATCTCCATTATTTCTTAATTTTTTTA  (Positions 465-
493 (inclusive) of SEQ ID NO. 5)
        Mut4     TTcgTaTCCATTAgTgCTTAATTTTTTTA  (SEQ ID NO:23)
        Mut5     TTcgTaTCCATTATTTCTTAATTTTTTTA  (SEQ ID NO:24)
        Mut6     TTAATCTCCATTAgTgCTTAATTTTTTTA  (SEQ ID NO:25)
```

B

| | | | | Mut4 | mut5 | mut6 |
|---|---|---|---|---|---|---|
| COMT1-422 Probe | + | + | + | + | + | + |
| xylem | - | + | + | + | + | + |
| WT competitor | - | - | + | - | - | - |
| Mut competitor | - | - | - | + | + | + |

SEQUENCE LISTING

<160> NUMBER OF SEQ ID NOS: 25

<210> SEQ ID NO 1
<211> LENGTH: 59
<212> TYPE: DNA
<213> ORGANISM: Populus tremuloides

<400> SEQUENCE: 1

```
taagttcagt aaatataatc gggtgaatat ctcatcatgt aattaaatat cttaatctc    59
```

<210> SEQ ID NO 2
<211> LENGTH: 16
<212> TYPE: DNA
<213> ORGANISM: Populus tremuloides

<400> SEQUENCE: 2

```
cattatttct taattt                                                  16
```

<210> SEQ ID NO 3
<211> LENGTH: 40
<212> TYPE: DNA
<213> ORGANISM: Populus tremuloides

<400> SEQUENCE: 3

```
tttttacttt aaattttttt atatacctga tatatatttt                        40
```

<210> SEQ ID NO 4
<211> LENGTH: 55
<212> TYPE: DNA
<213> ORGANISM: Populus tremuloides

<400> SEQUENCE: 4

```
ttttaaatat aacccatgat aaggaagttt tataaacctt tacctgcttg acata       55
```

<210> SEQ ID NO 5
<211> LENGTH: 978
<212> TYPE: DNA
<213> ORGANISM: Populus tremuloides

<400> SEQUENCE: 5

```
aagcttatac aatacataca atcaaacata tcaagaacct tgtgttttag aaaaaatcat    60
taaaaataaa tgaaaataaa agtagaaaat tgataaacat atataaatta taatatttga   120
cattacaaca atagcttttc tgattgtatt gaatgatttt gtctaccaaa atcaaatatt   180
cattcaatca aatgataata aaattatata gatatgaaat tgactaaata aaaaaaatta   240
tataatgtaa ggtcaacata ttagaaatac tatcaaaaaa taaatatttg tatatatata   300
acacatataa agatttaatt tatatggcgt gtgtttattc agtaaatttc atttgtatta   360
atttttaagt catgagtttt ataagatgtt gatttatctt ttattaattt aaataagttc   420
agtaaatata atcgggtgaa tatctcatca tgtaattaaa tatcttaatc tccattattt   480
cttaatttt tttatttttt tgttagttat tgttaatgat ttttttttatt tatataaatt   540
attattgatt tatttaatta gatatttgta taaattttta ctttaaattt ttttatatac   600
ctgatatata ttttttttaa atataaccca tgataaggaa gttttataaa cctttacctg   660
cttgacatag tacatcctgt tccaatagtc tcacctgaaa caggtttttt ttttttttttt   720
ttaaaaaaaa gagtttagca aataagaaga ggaaaaatat atagaagaaa aggtagggag   780
tcaggtctcg gaagaagcca tttgtgcatc aattagagag ttagaccaac cacaaggtgg   840
ttgagcactt caccatatat atcacccact ttccaacacc cttttcagta ttctcatatc   900
ctccgaaagc cttttcactt cctttcctta caccttcttc aacgttttgt ttccttgtag   960
aattcaatct cgatcaag                                                 978
```

<210> SEQ ID NO 6
<211> LENGTH: 1092
<212> TYPE: DNA

-continued

<213> ORGANISM: Populus tremuloides

<400> SEQUENCE: 6

| atgggttcaa | caggtgaaac | tcagatgact | ccaactcagg | tatcagatga | agaggcacac | 60 |
| ctctttgcca | tgcaactagc | cagtgcttca | gttctaccaa | tgatcctcaa | aacagccatt | 120 |
| gaactcgacc | ttcttgaaat | catggctaaa | gctggccctg | gtgctttctt | gtccacatct | 180 |
| gagatagctt | ctcacctccc | taccaaaaac | cccgatgcgc | tgtcatgtt  | agaccgtatc | 240 |
| ttgcgcctcc | tggctagcta | ctccattctt | acctgctctc | tgaaagatct | tcctgatggg | 300 |
| aaggttgaga | gactgtatgg | cctcgctcct | gtttgtaaat | tcttgaccaa | gaacgaggac | 360 |
| ggtgtctctg | tcagccctct | ctgtctcatg | aaccaggaca | aggtcctcat | ggaaagctgg | 420 |
| ttagtatcct | gtcttcacca | atctaagaaa | tcctgattta | catattgaat | ttgattataa | 480 |
| agtggcttac | aaactctcca | ctgagattta | tgttgttgca | catttgctct | gtttctcaat | 540 |
| cttattatgc | tatagaaaag | caatccaaag | tgaccaaatt | gagggatcgg | caccacagac | 600 |
| ttctctctca | ctagagacca | ttagagatgg | gtgaattagg | gtcccaccaa | tttgacaatt | 660 |
| gcaagccacc | actttccctg | ccataaaggt | tttgcctgcc | ggcaaatttg | tcgaccagtc | 720 |
| caaatgggca | tcccctaaag | ttctagtttt | aagagagaga | tatgattaga | atatttttct | 780 |
| acatatttaa | agttacttat | ggttaatgtc | cgaaaaaata | aaaaaatgaa | acatattgt  | 840 |
| tattgaattt | ttataaccat | caaacctacc | tctctaggtt | agaaatttcc | ttttcagcta | 900 |
| aaagaaattg | tattttccaa | tggtgatatt | aactgttatc | taaataaag  | tcaaattaat | 960 |
| atggtcaatt | attgctgtcg | atgctttatt | tatcaaatat | gaaccttcga | cgaaagcatc | 1020 |
| acttttttct | ctctctctca | aatttgagtc | ataaggatta | atggataggc | taattgccaa | 1080 |
| gaattaatta | ac | | | | | 1092 |

<210> SEQ ID NO 7
<211> LENGTH: 35
<212> TYPE: DNA
<213> ORGANISM: Artificial Sequence
<220> FEATURE:
<223> OTHER INFORMATION: Oligonucleotide

<400> SEQUENCE: 7
agttcagtaa atatcctagg gtgaatgctt catca       35

<210> SEQ ID NO 8
<211> LENGTH: 35
<212> TYPE: DNA
<213> ORGANISM: Artificial Sequence
<220> FEATURE:
<223> OTHER INFORMATION: Oligonucleotide

<400> SEQUENCE: 8
agttcagtaa atatcctagg gtgaatatct catca       35

<210> SEQ ID NO 9
<211> LENGTH: 35
<212> TYPE: DNA
<213> ORGANISM: Artificial Sequence
<220> FEATURE:
<223> OTHER INFORMATION: Oligonucleotide

<400> SEQUENCE: 9
agttcagtaa atataatcgg gtgaatgctt catca       35

<210> SEQ ID NO 10

```
<211> LENGTH: 35
<212> TYPE: DNA
<213> ORGANISM: Artificial Sequence
<220> FEATURE:
<223> OTHER INFORMATION: Oligonucleotide

<400> SEQUENCE: 10
agttcagtaa atataatcgg tcctatgctt catca                              35

<210> SEQ ID NO 11
<211> LENGTH: 35
<212> TYPE: DNA
<213> ORGANISM: Artificial Sequence
<220> FEATURE:
<223> OTHER INFORMATION: Oligonucleotide

<400> SEQUENCE: 11
agttcagtaa atatcctacg tcctatgctt catca                              35

<210> SEQ ID NO 12
<211> LENGTH: 35
<212> TYPE: DNA
<213> ORGANISM: Artificial Sequence
<220> FEATURE:
<223> OTHER INFORMATION: Oligonucleotide

<400> SEQUENCE: 12
agttcttcaa atatcctacg tcctatgctt catca                              35

<210> SEQ ID NO 13
<211> LENGTH: 34
<212> TYPE: DNA
<213> ORGANISM: Artificial Sequence
<220> FEATURE:
<223> OTHER INFORMATION: Oligonucleotide

<400> SEQUENCE: 13
tgaatgcctc atcatgtaac cacatgcctt aatc                              34

<210> SEQ ID NO 14
<211> LENGTH: 34
<212> TYPE: DNA
<213> ORGANISM: Artificial Sequence
<220> FEATURE:
<223> OTHER INFORMATION: Oligonucleotide

<400> SEQUENCE: 14
tgaatgcctc atcatgtaat taaatgcctt aatc                              34

<210> SEQ ID NO 15
<211> LENGTH: 34
<212> TYPE: DNA
<213> ORGANISM: Artificial Sequence
<220> FEATURE:
<223> OTHER INFORMATION: Oligonucleotide

<400> SEQUENCE: 15
tgaatgcctc atcatgtaac cacatatctt aatc                              34

<210> SEQ ID NO 16
<211> LENGTH: 34
<212> TYPE: DNA
<213> ORGANISM: Artificial Sequence
<220> FEATURE:
<223> OTHER INFORMATION: Oligonucleotide

<400> SEQUENCE: 16
```

-continued tgaatatctc atcatgtaac cacatatctt aatc                    34

<210> SEQ ID NO 17
<211> LENGTH: 34
<212> TYPE: DNA
<213> ORGANISM: Artificial Sequence
<220> FEATURE:
<223> OTHER INFORMATION: Oligonucleotide

<400> SEQUENCE: 17
tgaatatctc atcatgtaat taaatgcctt aatc                    34

<210> SEQ ID NO 18
<211> LENGTH: 34
<212> TYPE: DNA
<213> ORGANISM: Artificial Sequence
<220> FEATURE:
<223> OTHER INFORMATION: Oligonucleotide

<400> SEQUENCE: 18
tgaatgcctc atcatgtaat taaatatctt aatc                    34

<210> SEQ ID NO 19
<211> LENGTH: 34
<212> TYPE: DNA
<213> ORGANISM: Artificial Sequence
<220> FEATURE:
<223> OTHER INFORMATION: Oligonucleotide

<400> SEQUENCE: 19
tgcctgcttc atcatgtaat taaatatctt aatc                    34

<210> SEQ ID NO 20
<211> LENGTH: 34
<212> TYPE: DNA
<213> ORGANISM: Artificial Sequence
<220> FEATURE:
<223> OTHER INFORMATION: Oligonucleotide

<400> SEQUENCE: 20
tgcctgcttc atcatgtaac catagctgtt aatc                    34

<210> SEQ ID NO 21
<211> LENGTH: 34
<212> TYPE: DNA
<213> ORGANISM: Artificial Sequence
<220> FEATURE:
<223> OTHER INFORMATION: Oligonucleotide

<400> SEQUENCE: 21
tgcctgcttc tttctgtaat taaatatctt aatc                    34

<210> SEQ ID NO 22
<211> LENGTH: 34
<212> TYPE: DNA
<213> ORGANISM: Artificial Sequence
<220> FEATURE:
<223> OTHER INFORMATION: Oligonucleotide

<400> SEQUENCE: 22
tgcctgcttc atcatccttt taaatatctt aatc                    34

<210> SEQ ID NO 23
<211> LENGTH: 30
<212> TYPE: DNA
<213> ORGANISM: Artificial Sequence
<220> FEATURE:

```
<223> OTHER INFORMATION: Oligonucleotide

<400> SEQUENCE: 23
ttcgtatcca ttagtgctta attttttta                                               30

<210> SEQ ID NO 24
<211> LENGTH: 30
<212> TYPE: DNA
<213> ORGANISM: Artificial Sequence
<220> FEATURE:
<223> OTHER INFORMATION: Oligonucleotide

<400> SEQUENCE: 24
ttcgtatcca ttatttctta attttttta                                               30

<210> SEQ ID NO 25
<211> LENGTH: 30
<212> TYPE: DNA
<213> ORGANISM: Artificial Sequence
<220> FEATURE:
<223> OTHER INFORMATION: Oligonucleotide

<400> SEQUENCE: 25
ttaatctcca ttagtgctta attttttta                                               30
```

COMT1 GENE FIBER-SPECIFIC PROMOTER ELEMENTS FROM POPLAR

CROSS-REFERENCE TO RELATED APPLICATIONS

This application is a national stage filing under 35 U.S.C. 371 of International Application No. PCT/US2009/041956, filed on Apr. 28, 2009, which claims the benefit of priority to U.S. Provisional Patent Application Ser. No. 61/048,435, filed on Apr. 28, 2008, each of which is incorporated herein by reference in its entirety.

STATEMENT REGARDING FEDERAL SPONSORED RESEARCH OR DEVELOPMENT

This invention was supported in part by grant nos. OR22072-121 and EPA82947901-129. The United States government has certain rights in this invention.

BACKGROUND

Manipulation and control of the amounts and types of cellulose and lignin synthesized and deposited in plants and trees is of interest in the forestry, paper and biofuels industries. Tree species synthesize large quantities of lignin, particularly in and around the vascular tissues. Manipulating lignin and/or cellulose in plants and trees can prove beneficial by providing trees and plants with improved disease resistance, increased strength for use in construction, increased biomass usable as fuel or biofuel, improved digestibility (such as for forage crops), as well as having qualitative and quantitative variation in cellulose and/or lignin for paper processing. However, progress in this area has been impeded by difficulties in regulating gene expression in transgenic plants in tissue- or cell-type specific manners.

SUMMARY

In one embodiment, the invention provides a nucleic acid construct containing a fiber-specific element having at least 15 consecutive base pairs of SEQ ID NO: 1, or a reverse complement of at least 15 consecutive base pairs of SEQ ID NO: 1, operably connected to a promoter sequence not natively associated with SEQ ID NO: 1.

In another embodiment, the invention provides a nucleic acid construct containing two or more fiber-specific elements that each have at least 9 consecutive base pairs of SEQ ID NO: 1, or a reverse complement of at least 9 consecutive base pairs of SEQ ID NO: 1, operably connected to a promoter sequence not natively associated with SEQ ID NO: 1.

In a further embodiment, the invention provides a nucleic acid construct containing at least two fiber-specific elements operably connected to a promoter sequence. Each of fiber specific elements contain at least 9 consecutive base pairs of SEQ ID NO: 1, or a reverse complement of at least 9 consecutive base pairs of SEQ ID NO: 1, and are from partially or completely overlapping regions of SEQ ID NO: 1, or are the same.

In another embodiment, the invention provides a method of directing expression of a polypeptide to the fibers of a plant by transforming the plant with constructs containing fiber-specific elements of the invention.

Other aspects of the invention will become apparent by consideration of the detailed description and accompanying drawings.

BRIEF DESCRIPTION OF THE DRAWINGS

FIG. 1 is a schematic representation of the 59 base-pair sequence of SEQ ID NO: 1 which identifies elements within SEQ ID NO: 1 that may direct transcription of a polynucleotide to the fibers of a plant.

FIG. 5A is a schematic representation showing constructs used to make probes for use in an Electrophoretic Mobility Shift Assay. FIG. 5B is a photograph showing the results of an Electrophoretic Mobility Shift Assay FIG. 6A is a schematic representation showing constructs used to make probes for use in an Electrophoretic Mobility Shift Assay. FIG. 6B is a photograph showing the results of an Electrophoretic Mobility Shift Assay

DETAILED DESCRIPTION

Figure 2:
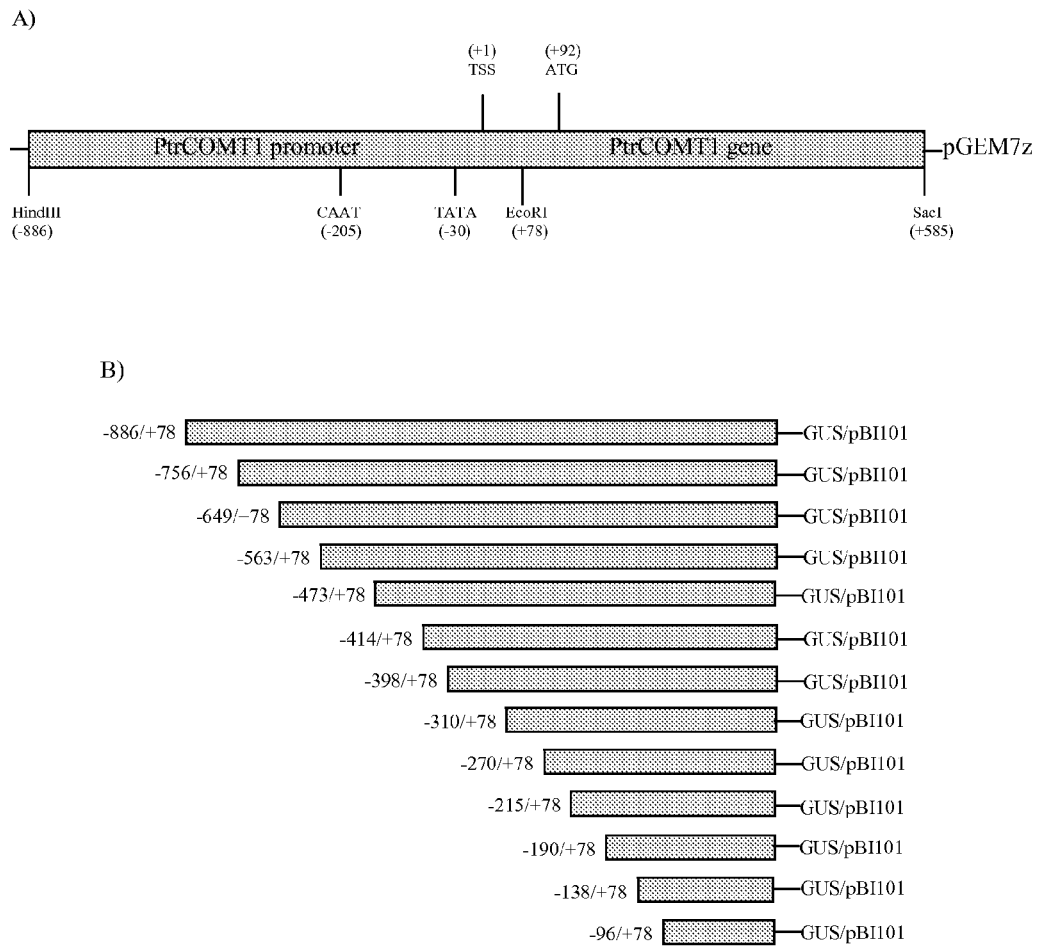
FIG. 2 is a schematic representation showing promoter deletion: GUS fusion constructs

Manipulation of the amounts and types of cellulose and lignin in plants is of importance in forestry, agriculture and paper processing. Preferably, expression of genes affecting biochemical pathways involved in the metabolism of lignin and cellulose is regulated with respect to particular tissues or regions of the plant, such as the vascular tissue and the plant fibers.

Specificity of expression in the plant fibers is particularly desirable for manipulating enzymes involved in lignin and cellulose biosynthesis. The fiber-specific elements of the instant invention can be used to express nucleotide sequences in vascular tissue and plant fibers to modify the content and composition of cellulose, thereby affecting plant growth and biomass characteristics. The biosynthesis of lignin and composition of lignin in the plant fibers may also be manipulated to produce plants or trees adapted for a particular end-use.

In one embodiment, the present invention provides a nucleotide construct that can be used to direct expression of a polypeptide to the fibers of a plant. The nucleotide construct contains a fiber-specific element and a promoter sequence not natively associated with the fiber-specific element. The construct can be used to develop other constructs including sequences encoding polypeptides ("coding sequences") that one wishes to specifically express in plant fibers. The coding sequence is operably linked to the promoter sequence to allow fiber-specific expression in plants into which the constructs are delivered. Optionally, the constructs may include features useful in gene cloning, including, but not limited to, unique restriction sites, multiple cloning sites, selectable markers, origins of replication, etc.

As described in the Examples below, a 59 base sequence (SEQ ID NO: 1), found upstream of the coding sequence of a *Populus tremuloides* caffeic acid O-methyltransferase I gene (PtrCOMT1), was discovered to direct fiber-specific expression of a GUS coding sequence.

SEQ ID NO: 1 corresponds to nucleotides of positions −473 to −413 of the positive DNA strand upstream of the transcription start site (TSS) of the PtrCOMPT1 gene, with position 1 of SEQ ID NO: 1 corresponding to position −473 upstream from the transcription start site. The transcription start site is 92 nucleotides upstream of the ATG translation start site, and begins at position 888 of SEQ ID NO. 5. SEQ ID NO: 1 is included within a 978 base sequence (SEQ ID NO:5) located upstream of the translation start site (ATG) of the PtrCOMT1 coding sequence (SEQ ID NO: 6), with position 1 of SEQ ID NO: 5 corresponding to position −886 of the sequence upstream from the transcription start site (TSS) of PtrCOMT1.

It is envisioned that subsequences of the sequence of SEQ ID NO:1 would be sufficient to serve as a fiber-specific element, provided that the subsequence have the ability to function with a promoter sequence to allow fiber-specific expression of a coding sequence or other polynucleotide operably linked to the promoter.

As used herein, a fiber-specific element is an element that, when associated with a promoter sequence, increases or causes fiber-specific expression of a coding sequence operably linked to the promoter sequence, relative to the expression of the coding sequence linked to a promoter sequence not associated with the element.

Fiber-specific expression means that expression of polynucleotides occurs predominantly in the plant fibers. Fiber-specific expression may be determined by operably connecting the promoter sequence and the fiber-specific element to a reporter sequence, such as a sequence encoding GUS (β-glucuronidase), and evaluating expression of the reporter sequence or polypeptide in the fibers, and other regions of the plant. One of skill in the art will appreciate that fiber-specific expression does not exclude the possibility that the reporter sequence or polypeptide may be expressed at relatively low levels in non-fiber parts of the plant.

As used herein, the fibers of a plant, or plant fibers, refers to one or more cells or cell types comprising the vascular tissue of the plant, including, for example, the xylem libriform fibers, xylem fiber tracheids and phloem fibers of angiosperms, and tracheids of gymnosperms. Constructs of the invention may be used to direct transcription of a polynucleotide in one or more of these cell types.

Suitably, a fiber specific element may comprise consecutive base pairs of SEQ ID NO:1, e.g., at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50 consecutive base pairs of SEQ ID NO: 1, or of a reverse complement of SEQ ID NO: 1.

In one embodiment, the fiber-specific element may be designed to contain one or more particular non-contiguous subsequences of SEQ ID NO: 1 and/or its reverse complement (designated the negative strand herein). These subsequences may work alone or in concert to target transcription and/or expression to the plant fibers.

Subsequences potentially suitable for use in a fiber-specific element are depicted in FIG. 1 and include a GTGA motif, (+ strand, positions 23-26 inclusive of SEQ ID NO: 1), one or more AT rich regions (+/− strand, positions 41-47, 10-19, 26-30, 40-50, and 52-56 (each inclusive) of SEQ ID NO: 1), YACT box (− strand, positions 8-11 inclusive of SEQ ID NO: 1), an *Arabidopsis* response regulator element (NGATT, where N is any nucleotide) (− strand, positions 17-21 and 54-58 inclusive of SEQ ID NO: 1), GTGA motif (− strand, positions 23-26 inclusive of SEQ ID NO: 1), one or more GATA boxes (− strand, positions 28-31 and 48-51 inclusive of SEQ ID NO: 1). Constructs of the invention may contain at least one, at least two, at least three, at least four, at least five, at least six or at least seven of these elements, and/or the reverse complement of the subsequences identified above, in any combination effective to direct fiber-specific expression. For example, the construct may contain, in the forward and/or reverse complement form, a GATA box, an *Arabidopsis* response regulator element and the AT-rich element, such as the element from positions 41-46 of SEQ ID NO: 1.

A construct according to the present invention may contain more than one fiber-specific element, for example, it may contain at least two, at least three, at least four, at least five, at least six, at least seven, at least eight, at least nine, at least ten, at least fifteen, or at least twenty, or more fiber-specific elements, which may include the same sequence, or non-identical overlapping or non-overlapping sequences within SEQ ID NO: 1, and/or the reverse complement of SEQ ID NO: 1. In one embodiment, the fiber-specific elements are present as tandem repeats. The inclusion of repeated sequences suitably enhances the specificity of expression of a nucleotide sequence, such as a coding sequence, to the plant fibers.

In addition to the fiber-specific elements of SEQ ID NO: 1, the constructs may include other sequences that enhance or alter transcription or expression of a polynucleotide. For example, the constructs may include at least 5, at least 6, at least 7, at least 8, at least 9, at least 10, at least 11, at least 12, at least 13, at least 14, or at least 15 consecutive base pairs of SEQ ID NO: 2, SEQ ID NO: 3, and/or SEQ ID NO: 4, or a reverse complement of SEQ ID NO: 2, SEQ ID NO: 3, and/or SEQ ID NO: 4. SEQ ID NO: 2 is from −414 to −398 base-pairs upstream of the transcription start site (TSS) of the PtrCOMT1 coding sequence. SEQ ID NO: 3 is from −310 to −270 base-pairs upstream of the TSS of the PtrCOMT1 coding sequence. SEQ ID NO: 4 is from −270 to −215 base-pairs upstream of the TSS of the PtrCOMT1 coding sequence. These elements of SEQ ID NO: 2-4 may be used alone or in combination with each other, and/or with the fiber-specific elements of SEQ ID NO: 1.

The constructs also contain a promoter sequence that is not natively associated with the fiber-specific element and which is operably connected to fiber-specific element, such that when the construct is introduced into a plant, transcription will occur specifically in plant fibers.

As used herein, a "promoter sequence" is intended to mean a nucleic acid that binds RNA polymerase, either directly or via transcription factors, and facilitates transcription of DNA to generate an mRNA molecule from a nucleic acid molecule that is operably linked to the promoter.

A promoter sequence not natively associated with the fiber-specific element may include any promoter sequence other than the promoter of PtrCOMT1. Suitable promoter sequences include, without limitation, the CaMV 35S minimal promoter, the NOS promoter from *Agrobacterium*, mannopine synthetase promoter, and sequences upstream of polynucleotides encoding enzymes of the cellulose synthesis pathway or phenylpropanoid pathway.

Other suitable promoter sequences not natively associated with the fiber-specific element may include modified PtrCOMT1 promoter sequences, i.e., promoter sequences that have been reconstituted to contain one or more sub-regions and/or altered regions of the ptrCOMPT1 sequence.

In some embodiments, the promoter sequence may include the native PtrCOMT1 sequence if the fiber-specific elements are repeated or are manipulated to be in a different position or orientation than is found in the native PtrCOMT1 sequence. This includes, for example, constructs in which two or more of the fiber-specific elements are from partially or completely overlapping regions of SEQ ID NO: 1, or are the same.

The one or more fiber-specific elements do not need to be directly connected to each other, to the promoter sequence, or to the polynucleotide to be transcribed, and the construct may contain nucleotides intervening between these sequences, while still being capable of directing expression of a polynucleotide to the plant fibers.

A construct according to the present invention may contain a particular desired polynucleotide to be transcribed that is operably connected to the promoter sequence. As used herein, "operably connected" with respect to the promoter sequence and the desired polynucleotide means that the promoter sequence can facilitate transcription of the desired nucleotide sequence to produce an RNA molecule under appropriate conditions. The RNA generated may code for a protein or polypeptide or may code for an RNA interfering, or antisense molecule. When the nucleotide sequence is a coding sequence, the polypeptide is suitably expressed.

The coding sequence or other polynucleotide to be transcribed may be any one where expression in the plant fibers is desirable. In one embodiment, the nucleotide sequence to be transcribed encodes a polypeptide that is an enzyme of the phenylpropanoid pathway, an enzyme in the G-lignin pathway, an enzyme in the S-lignin pathway, a cellulose synthase, a sucrose synthase, a cellulase, a transcription factor, an enzyme in phytohormone biosynthesis or a microtubule component. The polynucleotide may encode a polypeptide that regulates the synthesis of lignin or cellulose. In one embodiment, expression of the polypeptide in the plant fibers may be altered by varying external or environmental conditions.

Examples of polynucleotides that may be used to manipulate lignin content or composition in the plant fibers include those encoding one or more of cinnamyl alcohol dehydrogenase (CAD), cinnamate 4-hydroxylase (C4H), coumarate 3-hydroxylase (C3H), phenolase (PNL), caffeoyl-CoA O-methyl transferase (CCoAOMT), cinnamoyl-CoA reductase (CCR), phenylalanine ammonia-lyase (PAL), 4-coumarate:CoA ligase (4CL), peroxidase (PDX) coniferin β-glucosidase (CBG), hydroxycinnamoyl-CoA shikimate/quinate hydroxycinnamoyl transferase (HCT), and caffeic acid 3-O-methyltransferase (COMT).

When constructs are operably connected to DNA or RNA that encodes antisense RNA or interfering RNA, which corresponds to the coding sequence of a polypeptide of interest, a decreased amount of the polypeptide of interest may result. Polypeptides targeted for suppression include enzymes involved in lignin, cellulose, sucrose, phytohormone or microtubule metabolism as discussed above. The use of RNAi to inhibit gene expression in plants is specifically described in WO 99/61631, which is herein incorporated by reference in its entirety.

The present invention also provides vectors comprising the nucleic acid constructs. Numerous vectors have been described in the literature, many of which are commercially available. Suitable vectors include, for example, Ti-plasmids derived from the *A. tumefaciens*, and plasmids capable of replication in a bacterial host, such as *E. coli*. Additionally, vectors and constructs may include an origin of replication (replicons) for a particular host cell. Various prokaryotic replicons are known to those skilled in the art, and function to direct autonomous replication and maintenance of a recombinant molecule in a prokaryotic host cell.

A plasmid vector suitable for the introduction of nucleic acid of the current invention in monocots may contain, for example, in addition to the fiber-specific element and promoter region, an intron that provides a splice site to facilitate expression of the coding sequence (such as the Hsp70 intron; PCT Publication WO 93/19189); and a 3' polyadenylation sequence such as the nopaline synthase 3' sequence (NOS 3; Fraley et al. (1983) Proc Natl Acad Sci USA 80: 4803-4807). This expression cassette may be assembled on high copy replicons suitable for the production of large quantities of DNA.

An *Agrobacterium*-based plant transformation vector for use in transformation of dicotyledonous plants is plasmid vector pMON530 (Rogers et al. (1987) In Methods in Enzymology. Edited by R. Wu and L. Grossman. p 253-277. San Diego: Academic Press). Plasmid pMON530 is a derivative of pMON505 prepared by transferring the 2.3 kb StuI-HindIII fragment of pMON316 into pMON526. Another useful Ti plasmid cassette vector is pMON17227, described in PCT Publication WO 92/04449 (herein incorporated by reference in its entirety) and contains a sequence encoding an enzyme conferring glyphosate resistance fused to the *Arabidopsis* EPSPS chloroplast transit peptide.

Vectors and constructs of the invention may include a selectable marker so that transformed cells can be easily identified and selected from non-transformed cells. Examples of such markers include, but are not limited to, a neomycin phosphotransferase coding sequence, which confers kanamycin resistance; a bar coding sequence, which confers bialaphos resistance; a mutant EPSP synthase coding sequence, which confers glyphosate resistance; a nitrilase coding sequence, which confers resistance to bromoxynil; a mutant acetolactate synthase coding sequence, which confers imidazolinone or sulphonylurea resistance; and a methotrexate resistant DHFR coding sequence. Other selectable markers include, but are not limited to, those conferring resistance to hygromycin, tetracycline and ampicillin.

Various sequences used in the construct can be made by any suitable means, including, for example, joining synthesized oligonucleotides, joining fragments generated by PCR, or using cloning techniques.

The invention also provides host cells which comprise the vectors of the current invention. As used herein, a host cell refers to the cell in which the coding product is ultimately expressed. Accordingly, a host cell can be an individual cell, a cell culture or cells as part of an organism.

The invention further provides a method for generating plants in which the transcription of polynucleotides and/or expression of polypeptides is targeted or directed to the fibers of a plant. In one embodiment, the invention provides methods of directing expression of a polypeptide to the fibers of a plant by transforming the plant with vectors and/or constructs of the invention, such that expression of the polypeptide is targeted to the plant fibers.

Transformation of a plant may be carried out by introducing into a plant cell or plant vectors and/or constructs of the invention, to form a transformed or transgenic plant. If a plant cell is used, the plant may be subsequently regenerated from the plant cell. Methods for transforming plants and regenerating plants from plant cells are known. Suitable methods for transforming plants and trees include, without limitation, those disclosed Tsai C-J, Podila G K, Chiang V L (1994), Plant Cell Reports 14: 94-97; Han, K.-H., Meilan, R., Ma, C., and Strauss, S. H. (2000) Plant Cell Reports 19:315-320; and Meilan, R. and Ma, C. (2006) In: Methods in Molecular Biology, vol. 344:143-151; Kan Wang, Editor, *Agrobacterium* Protocols, 2/e, volume 2, Humana Press Inc., Totowa, N.J., and in U.S. Pat. No. 5,922,928, herein incorporated by reference in its entirety.

Plants transformed with vectors and/or constructs containing the fiber-specific elements are also provided. Any plant into which the constructs of the invention can be introduced and expression targeted to the plant fibers may be used. Suitable plants include, but are not limited to, woody plants, trees, crop plants and biofuel plants such as alfalfa, cotton, maize, rice, tobacco, grasses (such as switchgrass), aspen, poplar, cottonwood, pines (such as loblolly pine), sweetgum, eucalyptus, fir, maple, oak, willow and acacia plants. A "woody plant" is herein defined as a perennial plant whose stem comprises woody tissue. Examples of woody plants may include trees, shrubs or vines.

In one embodiment, plants transformed with a vector or construct of the invention, show expression or suppression of a polypeptide in one or more of the fibers in xylem and phloem of normal wood, tension wood (TW) and opposite wood (OW) of the plant, relative to a similar plant that has not been transformed with a vector or construct of the invention. A transformed or transgenic plant suitably produces altered (increased or decreased) amounts or ratios of lignin or cellulose, or produces lignin or cellulose of a different structure or type (such as S lignin, G lignin) compared with plants not expressing the polynucleotides.

It is to be understood that the invention is not limited in its application to the details of construction and the arrangement of components set forth in the following description or illustrated in the following drawings. The invention is capable of other embodiments and of being practiced or of being carried out in various ways.

EXAMPLES

Example 1

PtrCOMT1 Promoter Deletion:GUS Fusion Constructs and Aspen Transformation

Promoter deletion GUS fusion constructs were generated from a 1.5 Kb PtrCOMT1 promoter fragment cloned into the pGEM-7Z vector backbone and were used to transform aspen leaf discs. Thirteen PtrCOMT1 promoter deletion::GUS fusion constructs (depicted in FIG. 2) were transformed into Agrobacterium tumefaciens strain C58/pM90 by the freeze and thaw method. Positive transformants were confirmed using PCR and transferred to greenhouse pots for further analysis.

The thirteen 5'-unidirectional promoter deletion::GUS fusions were analyzed in transgenic aspen to examine PtrCOMT1 promoter activity during stem development. Under control of the −886/+78 fragment (hereafter referred to as the 'full-length' promoter), GUS activity was localized to the metaxylem and cambial zone, with faint staining in the cortex of internode 3. No staining was observed in the primary phloem. At internode 5, promoter activity was restricted to the vessels and developing xylem fibers surrounding the vessels. GUS staining was also observed in pith cells adjacent to the medullary sheath, but was absent in phloem and cortex. In stem internodes undergoing secondary thickening, GUS signal was observed in xylem and phloem fibers, visible at the 13th internode. GUS staining in xylem was absent in vessels and in newly formed fibers of the expanding zone, but preferentially localized to older, thick-walled fiber cells that also stained red with the Maule reagent, indicative of S-lignin deposition. These results suggest the involvement of PtrCOMT1 in S lignin biosynthesis.

Deletion of the promoter to −756 did not appear to affect its activity, but removal of an additional 107 by (to −649) abolished GUS staining Further deletion to 563 and −473 restored GUS staining in xylem and phloem fibers, similar to the pattern observed with the full length promoter. Deletion of an additional 59 by (−414) resulted in GUS staining in thin-walled vessels and fibers of the expanding xylem, cambial region and xylary rays, and a near loss of activity in phloem fibers. Deletion to −398 abolished GUS staining, but deletion to −310 restored weak staining in xylem and phloem fibers. The −270 fragment exhibited detectable promoter activity in our study, directing GUS in primary xylem, cambial zone, cortex and pith at young (third) internode. At older internodes, GUS staining was observed primarily in phloem fibers, and weakly in cortex, ray parenchyma and pith. Taken together, these results indicate that the PtrCOMT1 promoter has elements for both activation and repression of transcription.

Deletion from −756 to −649 resulted in loss of PtrCOMT1 promoter activity. Apart from WI, this region also contains a MYC binding site that partially overlaps an I-box. A 30 by oligo (−715 to −687) containing both MYC and I-box interacted strongly with xylem nuclear extracts but weakly with phloem nuclear proteins. Specificity of the binding was confirmed by competition with unlabeled oligos containing either wildtype or mutated MYC and I-box sequences. Labeled oligos containing another I-box element (−246 to −275) showed specific interaction with xylem-derived nuclear extracts. A xylem-specific gel retardation pattern was also detected using probes bearing the MYB1 element, a suspected negative regulator between −398 and −310. Deletion of this region restored GUS activity to the remaining 3' end of the fragment. Competition with a 100-fold molar excess of unlabeled wildtype oligo greatly reduced the binding signal, whereas competition with a similar amount of mutant oligo did not have an effect. EMSA experiments involving another MYB-binding site, MYB2, performed using the same amount of xylem nuclear extracts, showed an interaction. Finally, a DPBF-containing oligo also interacted strongly with xylem, but not phloem nuclear proteins, and the specificity of the interaction was validated by competition experiments. A GT-1 containing oligo (−149 and −120) showed weak interaction with xylem.

The PtrCOMT1 promoter directed GUS activity primarily to thick-walled fiber cells of xylem and phloem in aspen stems. Activities were also noted in non-lignifying cells of young internodes, including cortex, phloem, ray parenchyma and pith. The expression of PtrCOMT1 in thick-walled xylem fibers and its absence in newer, thin-walled fibers suggests a role for PtrCOMT1 in S lignin synthesis and a delay in S lignin deposition, relative to G lignin, during early stem development in angiosperms. COMT1 promoters were responsive to mechanical stress, with their activities becoming restricted to the tension wood side, and being expressed in all cell types. This pattern of expression suggests their likely involvement in synthesis of stress-induced phenylpropanoids, such as lignans in tension wood.

Promoter deletion analysis revealed that the minimum 3' fragment required to sustain the magnitude, tissue-specificity and gravitational responsiveness of PtrCOMT1 expression was −473, although a nominal level of activity could still be seen with the −270 promoter. Deletion of −473 to −414 (SEQ ID NO: 1) led to an unusual pattern of cambium and expanding xylem localized activity, and an ambiguous response to mechanical bending. Progressive deletion beyond −414 abolished, and then restored PtrCOMT1 activity (e.g., −398 and 310). The unusual activity pattern of −414 suggests that the −414 fragment (SEQ ID NO: 1) harbors evolutionary conserved core element(s) for regulating lignin biosynthesis. It is envisaged that the I-box between −270 and 215 confers basal PtrCOMT1 expression in xylem, and is bending-responsive.

A slight enhancement of GUS signal in xylem fiber cells with deletion −310 was observed. Two regions, −398/−310 and −649/−573, appeared to reduce PtrCOMT1 expression. A tissue-specific element may be present between −414 and −398 for directing expression in expanding xylem.

The region between −473 and −414 was found to contain one or more dominant fiber-specific elements. The TF-complex may hinder TF interaction with the adjacent, expanding xylem-specific element at −398/−414, by virtue of their proximity. Its deletion would relieve the hindrance, thus enabling expression in expanding xylem as seen with −414. The region between −756 and −649 contains a MYC box, an I-box, a WI box and a GATA-box, all of which were confirmed to interact specifically with xylem-derived nuclear proteins. Putative cis elements located upstream of −756 or downstream of −215 did not appear to affect PtrCOMT1 expression, although downstream MYC (−195 and −88) and MYB2 (−115 and −61) elements also exhibited binding with xylem nuclear extracts. These elements may confer bending-induced activity in pith, as seen with −270.

PtrCOMT1 promoter activity was mainly found in thick-walled xylem fibers and was responsive to mechanical stress with its activity becoming restricted to the tension wood side. The minimum promoter sequence capable of sustaining Ptr-COMT1 tissue-specific and gravistimulated expression was −473, although basal level of activity could be seen with the −270 fragment.

Example 2

Electrophoretic Mobility Shift Assays (EMSA)

EMSA was performed using nuclear protein prepared from xylem, phloem and leaf tissues. Binding reactions were carried out for 30 minutes at room temperature. Each 25 µl binding reaction contained 1 pmol/µl of oligonucleotide probe with the promoter target sequence labeled with the infrared fluorophore IRDye700 (Licor biosciences, Lincoln, Nebr.), 10 µg nuclear proteins in 1× binding buffer (10 mM Tris-HCl, pH 7.5, 1 mM EDTA, 1 mM DTT, 60% glycerol, 2 µg poly (dI·dC) and 0.5 mM PMSF. For competition experiments, unlabeled oligonucleotides were added with a 50-100-fold molar excess ratio relative of the probe. The reaction mixture was electrophoresed at 4° C. on a 4% native polyacrylamide gel run at 50V for 2 hours in Tris-glycine buffer (25 mM Tris-HCl, 250 mM glycine and 1 mM EDTA, pH 8.5). After electrophoresis, the gel was analyzed using the Odyssey infrared imaging scanner (Licor Inc.)

In a first competition experiment, a probe containing the polynucleotide from position 2 to position 34 of SEQ ID NO. 1 (inclusive) was generated, and the sequence was mutated to provide six additional probes, as shown in FIG. 5A (SEQ ID NOs: 7-12). Results of the competition assay are shown in FIG. 5B. Competition was abolished when SEQ ID NO: 11 and 12 were used.

In a second competition experiment, a probe from position 24 to position 57 of SEQ ID NO. 1 (inclusive) was generated, and the sequence was mutated to provide ten additional probes, as shown in FIG. 6A (SEQ ID NOs: 13-22). Results of the competition assay are shown in FIG. 6B. Competition was abolished when probes containing SEQ ID NOs: 13, 15 and 20 were used.

Figure 7:
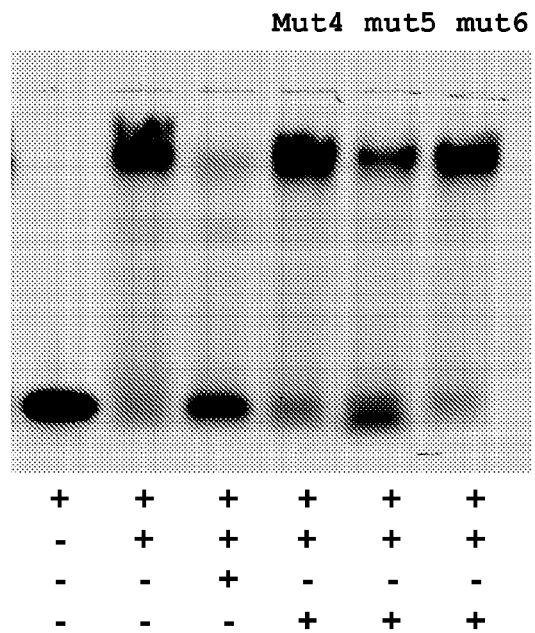
FIG. 7A is a schematic representation showing constructs used to make probes for use in an Electrophoretic Mobility Shift Assay.
FIG. 7B is a photograph showing the results of an Electrophoretic Mobility Shift Assay

In a third competition experiment, a probe from position 465 to position 493 of SEQ ID NO. 5 (inclusive) was generated, and the sequence was mutated to provide three additional probes, as shown in FIG. 7A (SEQ ID NOs: 23-25). Results of the competition assay are shown in FIG. 7B. Competition was least effective when the probe containing SEQ ID NO: 23 was used.

The region from and surrounding position 478 to position 482 (inclusive) of SEQ ID NO. 5 (TTTCT), and/or the reverse complement, may be important for targeting to "stem cell" type (meristemic) cells such as cambia and newly formed xylem cells.

Example 3

Transformation of Plants with Constructs Containing Fiber-specific Elements

Figure 3:
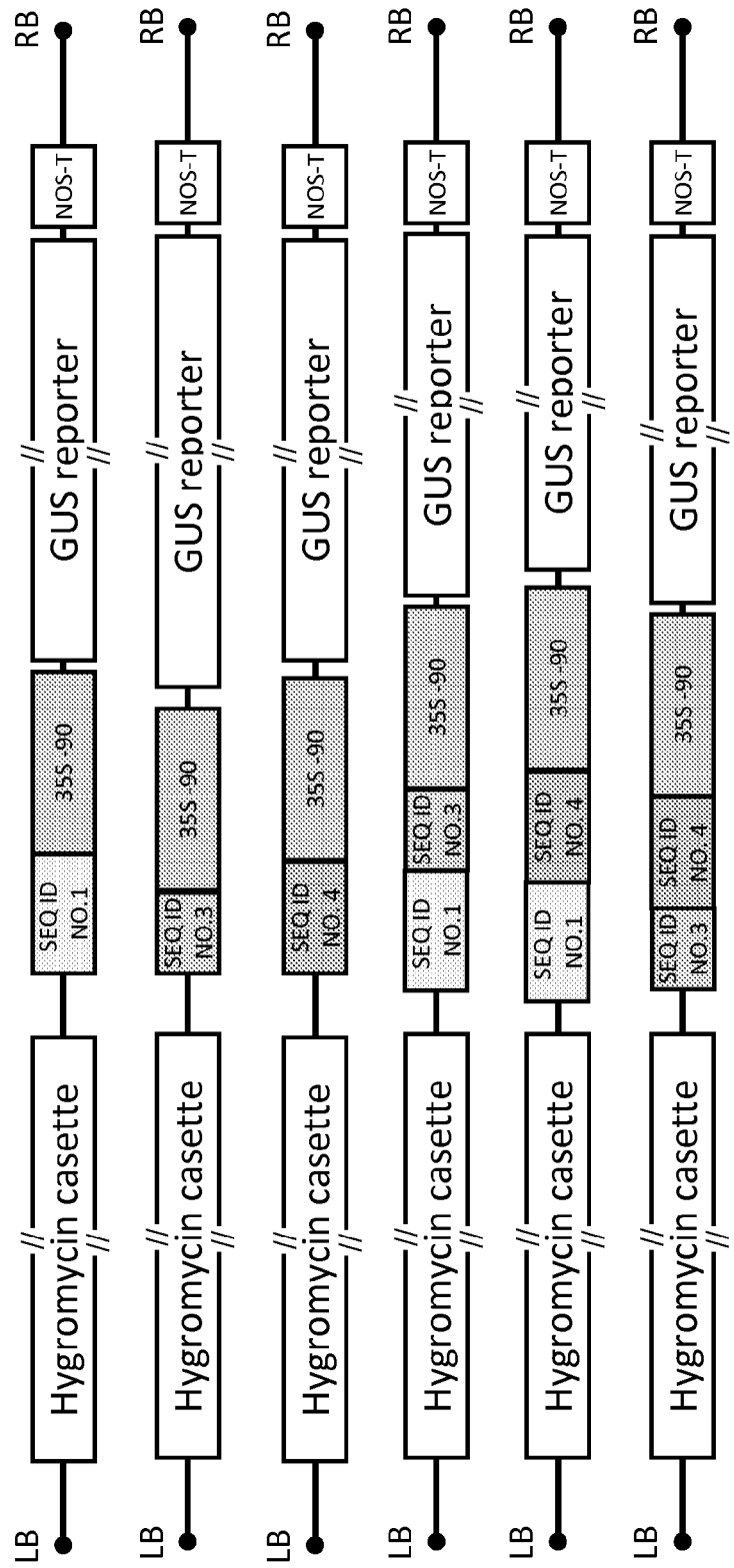
FIG. 3 is a schematic representation showing constructs containing fiber-specific elements operably connected to a promoter element and a polynucleotide encoding a GUS reporter polypeptide.
Figure 4:
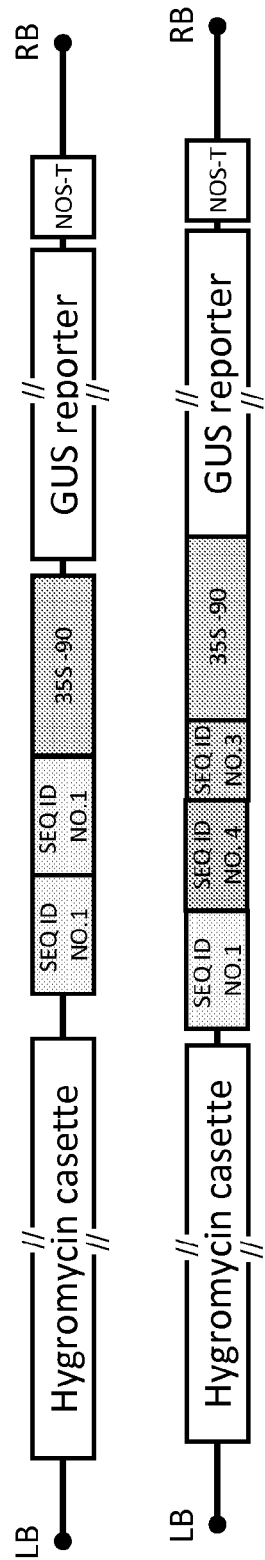
FIG. 4 is a schematic representation showing constructs containing fiber-specific elements operably connected to a promoter element and a polynucleotide encoding a GUS reporter polypeptide.

Constructs were formed having a hygromyacin cassette, the minimal 35S promoter and a polynucleotide encoding the GUS reporter polypeptide. The construct contained various combinations of SEQ ID NOs. 1, 3 and 4, as shown in FIGS. 3 and 4. The constructs shown in FIG. 3 were used to transform aspen plants. Fiber-specific expression of the GUS reporter polynucleotide in the fibers of the aspen plants is expected.

It is specifically contemplated that any embodiment of any method or composition of the invention may be used with any other method or composition of the invention. As used in this specification and the appended claims, the singular forms "a," "an," and "the" include plural referents unless the content clearly dictates otherwise. Thus, for example, reference to a composition containing "a conjugate" includes a mixture of two or more conjugates. It should also be noted that the term "or" is generally employed in its sense including "and/or" unless the content clearly dictates otherwise.

It also is specifically understood that any numerical value recited herein includes all values from the lower value to the upper value, i.e., all possible combinations of numerical values between the lowest value and the highest value enumerated are to be considered to be expressly stated in this application. For example, if a range is stated as 1% to 50%, it is intended that values such as 2% to 40%, 10% to 30%, or 1% to 3%, etc., are expressly enumerated in this specification.

Various features and advantages of the invention are set forth in the following claims.

What is claimed is:

1. A nucleic acid construct comprising a first fiber-specific element having at least 15 consecutive base pairs of SEQ ID NO: 1 or a reverse complement of at least 15 consecutive base pairs of SEQ ID NO: 1 operably connected to a promoter sequence not natively associated with the first fiber-specific element.

2. The construct of claim 1, further comprising a polynucleotide encoding a polypeptide operably connected to the promoter sequence.

3. The construct of claim 2, wherein the polypeptide is selected from an enzyme in the G-lignin pathway, an enzyme in the S-lignin pathway, a cellulose synthase, a sucrose synthase, a cellulase, a transcription factor, an enzyme in phytohormone biosynthesis and a microtubule component.

4. The construct of claim 1, further comprising a second fiber-specific element having at least 5 consecutive base pairs of SEQ ID NO: 1.

5. The construct of claim 4, wherein the first and second fiber-specific elements are from non-overlapping regions of SEQ ID NO: 1.

6. The construct of claim 4, wherein the first and second fiber-specific elements are from partially or completely overlapping regions of SEQ ID NO: 1, or are the same.

7. The construct of claim 1, wherein the construct comprises SEQ ID NO: 1.

8. The nucleic acid construct of claim 1, wherein the first fiber-specific element comprises a GATA box, an *Arabidopsis* response regulator element (NGATT), a GTGA box, an AT-rich element of at least 5 base-pairs, or a combination thereof.

9. The nucleic acid construct of claim 1, wherein the first fiber-specific element comprises a GATA box, a *Arabidopsis* response regulator element (NGATT), a GTGA element, and an AT-rich element of at least 5 base pairs.

10. The nucleic acid construct of claim 1, further comprising a second fiber-specific element having at least 9 consecutive base pairs of SEQ ID NO: 1 or a reverse complement of at least 9 consecutive base pairs of SEQ ID NO: 1.

11. The construct of claim 10, wherein the first and second fiber-specific elements are from non-overlapping regions of SEQ ID NO: 1.

12. The construct of claim 10, further comprising a third fiber-specific element having at least 5 consecutive base pairs of at least one of SEQ ID NO: 1, SEQ ID NO: 2, SEQ ID NO: 3, or SEQ ID NO: 4, or the reverse complements of at least 5 consecutive base pairs of at least one of SEQ ID NO: 1, SEQ ID NO: 2, SEQ ID NO: 3, or SEQ ID NO: 4.

13. The construct of claim 10, wherein the first or second fiber-specific element is repeated.

14. The construct of claim 10, further comprising a polynucleotide encoding a polypeptide operably connected to the promoter sequence.

15. The construct of claim 10, wherein the polypeptide is selected from an enzyme in the G-lignin pathway, an enzyme in the S-lignin pathway, a cellulose synthase, a sucrose synthase, a cellulase, a transcription factor, an enzyme in phytohormone biosynthesis and a microtubule component.

16. A nucleic acid construct comprising a first fiber-specific element having at least 9 consecutive base pairs of SEQ ID NO: 1 or a reverse complement of at least 9 consecutive base pairs of SEQ ID NO: 1, a second fiber-specific element having at least 9 consecutive base pairs of SEQ ID NO: 1 or a reverse complement of at least 9 consecutive base pairs of SEQ ID NO: 1 and a third fiber-specific element having at least 9 consecutive base pairs of SEQ ID NO: 1 or a reverse complement of at least 9 consecutive base pairs of SEQ ID NO: 1 operably connected to a promoter sequence, the first, and second and third fiber-specific elements being from partially or completely overlapping regions of SEQ ID NO: 1, being the same, or a combination thereof.

17. The construct of claim 16, further comprising a polynucleotide encoding a polypeptide operably connected to the promoter sequence.

18. A method of directing expression of a polynucleotide to the fibers of a plant comprising transforming the plant with the construct of claim 2.

19. The method of claim 18, wherein the plant is a tree.

20. The method of claim 18, wherein the polynucleotide encodes a polypeptide selected from an enzyme in the G-lignin pathway, an enzyme in the S-lignin pathway, a cellulose synthase, a sucrose synthase, a cellulose, a transcription factor, a phytohormone and a microtubule component.

21. A plant produced by the method of claim 18.

* * * * *

UNITED STATES PATENT AND TRADEMARK OFFICE
CERTIFICATE OF CORRECTION

PATENT NO. : 8,536,406 B2  Page 1 of 1
APPLICATION NO. : 12/990001
DATED : September 17, 2013
INVENTOR(S) : Tsai et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 277 days.

Signed and Sealed this

Fifteenth Day of September, 2015

Michelle K. Lee
*Director of the United States Patent and Trademark Office*